US010647771B2

(12) United States Patent
Yearley et al.

(10) Patent No.: US 10,647,771 B2
(45) Date of Patent: May 12, 2020

(54) ANTIBODY THAT BINDS TO HUMAN PROGRAMMED DEATH LIGAND 2 (PD-L2) AND USES THEREOF

(71) Applicant: Merck Sharp & Dohme Corp., Rahway, NJ (US)

(72) Inventors: Jennifer H. Yearley, San Jose, CA (US); Linda Liang, Mountain View, CA (US); Michael Eric Bigler, Redwood City, CA (US); Christopher John Gibson, Kennett Square, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 122 days.

(21) Appl. No.: 15/761,262

(22) PCT Filed: Sep. 20, 2016

(86) PCT No.: PCT/US2016/052569
§ 371 (c)(1),
(2) Date: Mar. 19, 2018

(87) PCT Pub. No.: WO2017/053250
PCT Pub. Date: Mar. 30, 2017

(65) Prior Publication Data
US 2018/0258171 A1    Sep. 13, 2018

Related U.S. Application Data

(60) Provisional application No. 62/221,472, filed on Sep. 21, 2015.

(51) Int. Cl.
*C07K 16/28* (2006.01)
*A61K 39/395* (2006.01)
*A61P 35/00* (2006.01)
*G01N 33/574* (2006.01)

(52) U.S. Cl.
CPC ........ *C07K 16/2827* (2013.01); *A61K 39/395* (2013.01); *A61P 35/00* (2018.01); *G01N 33/57492* (2013.01); *C07K 2317/20* (2013.01); *C07K 2317/52* (2013.01); *C07K 2317/56* (2013.01); *C07K 2317/565* (2013.01); *C07K 2317/567* (2013.01); *C07K 2317/76* (2013.01); *G01N 2333/4704* (2013.01)

(58) Field of Classification Search
None
See application file for complete search history.

(56) References Cited

U.S. PATENT DOCUMENTS

| | | |
|---|---|---|
| 9,073,994 B2 | 7/2015 | Honjo et al. |
| 2008/0118511 A1 | 5/2008 | Freeman et al. |
| 2014/0234296 A1 | 8/2014 | Sharma et al. |
| 2015/0197571 A1 | 7/2015 | Freeman et al. |

FOREIGN PATENT DOCUMENTS

| | | |
|---|---|---|
| WO | 2010036959 A2 | 4/2010 |
| WO | WO2014100079 A1 | 6/2014 |
| WO | 2014151006 A2 | 9/2014 |
| WO | WO2015088847 A1 | 6/2015 |
| WO | WO2015119923 A1 | 8/2015 |
| WO | 2016144673 A1 | 9/2016 |

OTHER PUBLICATIONS

Mariuzza, R.A. etal. The Structural Basis of Antigen-Antibody Recognition1 Annu. Rev. Biophys. Biphys. Chem. 16:139-159, 1987.*
Maccallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Goel et al. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
Brahmer et al., Safety and Activity of Anti-PD-L1 Antibody in Patients with Advanced Cancer, The New England Journal of Medicine, 2012, pp. 2455-3465, vol. 366, No. 26.
Cheah et al., Targeting the programmed death-1/programmed death-ligand 1 axis in lymphoma, Current Opinion Oncology, 2015, pp. 384-391, vol. 27, No. 5.
D. M. Pardoll, The blockade of immune checkpoints in cancer immunotherapy, Nature Reviews/Cancer, 2012, pp. 252-264, vol. 12.
Garon et al., Pembrolizumab for the Treatment of Non-Small-Cell Lung Cancer, The New England Journal of Medicine, 2015, pp. 2018-2028, vol. 372, No. 21.
Hamid et al., Safety and Tumor Responses with Lambrolizumab (Anti-PD-1) in Melanoma, New Eng. J. Med., 2013, 134-144, 369(2).

(Continued)

*Primary Examiner* — Nora M Rooney
(74) *Attorney, Agent, or Firm* — Letitia Walker; Laura M. Ginkel

(57) ABSTRACT

The present disclosure provides antibodies and antigen binding fragments thereof including, but not limited to, monoclonal antibodies that specifically bind to human programmed death ligand 2 (PD-L2). The invention further provides nucleic acids encoding the antibodies and antigen binding fragments of the invention and host cells transformed therewith. The antibodies and antigen binding proteins of the invention are useful in methods for the immunohistochemical detection of human PD-L2 expression in tissue samples.

18 Claims, 8 Drawing Sheets
Specification includes a Sequence Listing.

(56) References Cited

OTHER PUBLICATIONS

J. Yearley, https://www.youtube.com/watch?v=PHRbfz1RTHQ, PD-L2 expression and its relevance to anti-PD-1 therapy in cancer, Published on Nov 20, 2015.

Latchman et al., PD-L2 is a second ligand for PD-1 and inhibits T cell activation, Nature Immunology, 2001, pp. 261-268, vol. 2, No. 3.

Lesterhuis et al., Platinum-based drugs disrupt STAT6-mediated suppression of immune responses against cancer in humans and mice, The Journal of Clinical Investigation, 2011, pp. 3100-3108, vol. 121, No. 8.

Lesterhuis et al., PD-L2 is predominantly expressed by Th2 cells, Molecular Immunology, 2011, pp. 1-3, vol. 49.

Messal et al., PD-L2 is expressed on activated human T cells and regulates their function, Molecular Immunology, 2011, pp. 2214-2219, vol. 48.

Robert et al., Anti-programmed-death-receptor-1 treatment with pembrolizumab in ipilimumab-refractory advanced melanoma: a randomised dose-comparison cohort of a phase 1 trial, The Lancet, 2014, pp. 1109-1117, vol. 384.

Robert et al., Nivolumab in Previously Untreated Melanoma without BRAF Mutation, The New England Journal of Medicine, 2015, pp. 320-330, vol. 372, No. 4.

Robert et al., Pembrolizumab versus Ipilimumab in Advanced Melanoma, The New England Journal of Medicine, Jun. 25, 2015, pp. 2521-2532, 372.

Rodig et al., Endothelial expression of PD-L1 and PD-L2 down-regulates CD8+ T cell activation and cytolysis, Eur. J. Immunol., 2003, pp. 3117-3126, vol. 33.

Schmid et al., Association of PD-L2 expression in human tumors with atezolizumab activity., Tumor Biology, 2016, Abstract 110506.

Schuurman et al., The inter-heavy chain disulfide bonds of IgG4 are in equilibrium with intra-chain disulfide bonds, Molecular Immunology, 2001, pp. 1-8, vol. 38.

Taube et al., Association of PD-1, PD-1 ligands, and other features of the tumor immune microenvironment with response to anti-PD-1 therapy, Clinical Cancer Research, 2014, pp. 5064-5074, vol. 20.

Topalian et al., Safety, Activity, and Immune Correlates of Anti-PD-1 Antibody in Cancer, New Eng. J. Med., 2012, 2443-2454, 366(26).

Topalian et al., Survival, Durable Tumor Remission, and Long-Term Safety in Patients With Advanced Melanoma Receiving Nivolumab, Clinical Journal of Oncology, 2014, pp. 1020-1030, vol. 32, No. 10.

Wolchok et al, Nivolumab plus Ipilimumab in Advanced Melanoma, The New England Journal of Medicine, 2013, pp. 122-133, vol. 369(2).

Yearley et al., PD-L2 expression in human tumors: relevance to anti-PD-1 therapy in cancer, Late-Breaking Abstracts, 2015, pp. S718.

Schultheis, AM et al, PD-L1 expression in small cell neuroendocrine carcinomas, European Journal of Cancer, 2015, 421-426, vol. 51, No. 3.

Shi, M, Expression of Programmed Cell Death 1 Ligand 2 (PD-L2) is a Distinguishing Feature of Primary Mediastinal (Thymic) Large B-cell Lymphoma and Associated with PDCD1LG2 Copy Gain, The American Journal of Surgical Pathology, 2014, 1715-1723, vol. 38, No. 12.

* cited by examiner

Light chain: DNA sequence (399 bp)

[ATGGAATCACAGACCCAGGTCCTCATGTTTCTTCTGCTCTGGGTATCTGGTGCCTGTGCA]GA
CATTGTGATGACACAGTCTCCATCCTCCCTGGCTACGTCAGTAGGACAGAGGGTCACTATGAGC
TGCAAGTCCAGTCAGAACCTTTTATATAGTACCGATCAAAAGAACTATTTGGCCTGGTTCCAGC
AGAAACCAGGACAGTCTCCTAAACTTCTACTATACTTTGCATCCATTAGGGAATCTGGGGTCCC
TGATCGCTTCATAGGCAGTGGATCTGGGACAGATTTCACTCTTACCATCAGCAGTGTGCAGGCT
GAAGACCTGGCAGATTACTTCTGTCAGCAGCATTATAACACTCCTCCGACGTTCGGTGGAGGCA
CCAGACTGGAAATCAAA (SEQ ID NO:17)

Light chain: Amino acid sequence (133 AA)

[MESQTQVLMFLLLWVSGACA]DIVMTQSPSSLATSVGQRVTMSCKSSQNLLYSTDQKNYLAWF
QQKPGQSPKLLLYFASIRESGVPDRFIGSGSGTDFTLTISSVQAEDLADYFCQQHYNTPPTFGG
GTRLEIK (SEQ ID NO:19)

Heavy chain: DNA sequence (408 bp)

[ATGAACTTCGGGCTCAGCTTGATTTTCCTTGCCCTCATTTTAAAAGGTGTCCAGTGT]GAGGT
GCAGCTGGTGGAGTCTGGGGGAGACTTAGTGAAGTCTGGAGGGTCCCTGAAACTCTCCTGTGCC
GCCTCTGGATTCATTTTCAGTAGCTTTGGCATGTCTTGGGTTCGCCAGACTCCAGACAAGAGGC
TGGAGTGGGTCGCAACCATTAGTAGTGGTGGAAGGAATATCTACTATTTAGACAGTGTGAAGGG
GCGATTCACCATCTCCAGAGACAATGTCAAGAACATCCTGTACCTGCAAATGAGCGGTCTGAAG
TCTGAGGACTCAGCCATGTACTACTGTGCAAGAGAGGGGCACTATGCTTTGGACTACTGTGGTC
AAGGAACTTCAGTCACCGTCTCCTCA (SEQ ID NO:18)

Heavy chain: Amino acid sequence (136 AA)

[MNFGLSLIFLALILKGVQC]EVQLVESGGDLVKSGGSLKLSCAASGFIFSSFGMSWVRQTPDK
RLEWVATISSGGRNIYYLDSVKGRFTISRDNVKNILYLQMSGLKSEDSAMYYCAREGHYALDYC
GQGTSVTVSS (SEQ ID NO:20)

FIG.1

| Characteristic | Total N=172 |
|---|---|
| Age years median (range) | 60 (37–84) |
| Male | 143 (83.1) |
| Race | |
|   White | 129 (75.0) |
|   Asian | 27 (15.7) |
|   Other | 16 (9.3) |
| ECOG performance status | |
|   0 | 49 (28.5) |
|   1 | 123 (71.5) |
| Metastatic Staging | |
|   MX | 1 (0.6) |
|   M0 | 25 (14.5) |
|   M1 | 146 (84.9) |
| HPV status | |
|   Positive | 57 (33.1) |
|   Negative | 113 (65.7) |
|   Unknown | 2 (1.2) |
| Sum of target lesions at baseline mm median (range)[a] | 99.2 (10–664) |
| Previous adjuvant and/or neoadjuvant therapy | |
|   Yes | 81 (47.1) |
| No. of previous lines of therapy for recurrent or metastatic disease | |
|   0 | 32 (18.6) |
|   1 | 36 (20.9) |
|   2 | 40 (23.3) |
|   3 | 30 (17.4) |
|   4 | 19 (11.0) |
|   ≥5 | 15 (8.7) |
| [a] n=157 | |

FIG.6

| Status | Total | Non-responder | Responder | Response[a], % (CI) |
|---|---|---|---|---|
| PD-L1⁻ | 20 | 19 | 1 | 5.0 (0.1, 24.9) |
| PD-L1⁺ | 126 | 97 | 29 | 23.0 (16.0, 31.4) |
| PD-L2⁻ | 52 | 47 | 5 | 9.6 (3.2, 21.0) |
| PD-L2⁺ | 94 | 69 | 25 | 26.6 (18.0, 36.7) |
| PD-L1⁻/PDL-2⁻ | 17 | 16 | 1 | 5.9 (0.1, 28.7) |
| PD-L1⁺/PDL-2⁻ | 35 | 31 | 4 | 11.4 (3.2, 26.7) |
| PD-L1⁻/PDL-2⁺ | 3 | 3 | 0 | 0.0 (0.0, 70.8) |
| PD-L1⁺/PDL-2⁺ | 91 | 66 | 25 | 27.5 (18.6, 37.8) |
| [a]Full analysis set population. Positive (+) = ≥1% staining; negative (−) = <1% staining | | | | |

FIG.7

SEQUENCE LISTING

<160> NUMBER OF SEQ ID NOS: 22

<210> SEQ ID NO 1
<211> LENGTH: 23
<212> TYPE: PRT
<213> ORGANISM: Mus Musculus

<400> SEQUENCE: 1

Asp Ile Val Met Thr Gln Ser Pro Ser Ser Leu Ala Thr Ser Val Gly
1               5                   10                  15

Gln Arg Val Thr Met Ser Cys
            20

<210> SEQ ID NO 2
<211> LENGTH: 17
<212> TYPE: PRT
<213> ORGANISM: Mus Musculus

<400> SEQUENCE: 2

Lys Ser Ser Gln Asn Leu Leu Tyr Ser Thr Asp Gln Lys Asn Tyr Leu
1               5                   10                  15

Ala

<210> SEQ ID NO 3
<211> LENGTH: 15
<212> TYPE: PRT
<213> ORGANISM: Mus Musculus

<400> SEQUENCE: 3

Trp Phe Gln Gln Lys Pro Gly Gln Ser Pro Lys Leu Leu Leu Tyr
1               5                   10                  15

<210> SEQ ID NO 4
<211> LENGTH: 7
<212> TYPE: PRT
<213> ORGANISM: Mus Musculus

<400> SEQUENCE: 4

Phe Ala Ser Ile Arg Glu Ser
1               5

<210> SEQ ID NO 5
<211> LENGTH: 32
<212> TYPE: PRT
<213> ORGANISM: Mus Musculus

<400> SEQUENCE: 5

Gly Val Pro Asp Arg Phe Ile Gly Ser Gly Ser Gly Thr Asp Phe Thr
1               5                   10                  15

Leu Thr Ile Ser Ser Val Gln Ala Glu Asp Leu Ala Asp Tyr Phe Cys
            20                  25                  30

<210> SEQ ID NO 6
<211> LENGTH: 9
<212> TYPE: PRT
<213> ORGANISM: Mus Musculus

<400> SEQUENCE: 6

Gln Gln His Tyr Asn Thr Pro Pro Thr
1               5

<210> SEQ ID NO 7
<211> LENGTH: 10
<212> TYPE: PRT
<213> ORGANISM: Mus Musculus

<400> SEQUENCE: 7

Phe Gly Gly Gly Thr Arg Leu Glu Ile Lys
1               5                   10

<210> SEQ ID NO 8
<211> LENGTH: 113
<212> TYPE: PRT
<213> ORGANISM: Mus Musculus

<400> SEQUENCE: 8

Asp Ile Val Met Thr Gln Ser Pro Ser Ser Leu Ala Thr Ser Val Gly
1               5                   10                  15

Gln Arg Val Thr Met Ser Cys Lys Ser Ser Gln Asn Leu Leu Tyr Ser
            20                  25                  30

Thr Asp Gln Lys Asn Tyr Leu Ala Trp Phe Gln Gln Lys Pro Gly Gln
        35                  40                  45

Ser Pro Lys Leu Leu Leu Tyr Phe Ala Ser Ile Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asn Thr Pro Pro Thr Phe Gly Gly Gly Thr Arg Leu Glu Ile
            100                 105                 110

Lys

<210> SEQ ID NO 9
<211> LENGTH: 30
<212> TYPE: PRT
<213> ORGANISM: Mus Musculus

<400> SEQUENCE: 9

Glu Val Gln Leu Val Glu Ser Gly Gly Asp Leu Val Lys Ser Gly Gly
1               5                   10                  15

Ser Leu Lys Leu Ser Cys Ala Ala Ser Gly Phe Ile Phe Ser
            20                  25                  30

<210> SEQ ID NO 10
<211> LENGTH: 5
<212> TYPE: PRT
<213> ORGANISM: Mus Musculus

<400> SEQUENCE: 10

Ser Phe Gly Met Ser
1               5

<210> SEQ ID NO 11
<211> LENGTH: 14
<212> TYPE: PRT
<213> ORGANISM: Mus Musculus

<400> SEQUENCE: 11

Trp Val Arg Gln Thr Pro Asp Lys Arg Leu Glu Trp Val Ala
1               5                   10

<210> SEQ ID NO 12
<211> LENGTH: 17
<212> TYPE: PRT
<213> ORGANISM: Mus Musculus

<400> SEQUENCE: 12

Thr Ile Ser Ser Gly Gly Arg Asn Ile Tyr Tyr Leu Asp Ser Val Lys
1               5                   10                  15

Gly

<210> SEQ ID NO 13
<211> LENGTH: 32
<212> TYPE: PRT
<213> ORGANISM: Mus Musculus

<400> SEQUENCE: 13

Arg Phe Thr Ile Ser Arg Asp Asn Val Lys Asn Ile Leu Tyr Leu Gln
1               5                   10                  15

Met Ser Gly Leu Lys Ser Glu Asp Ser Ala Met Tyr Tyr Cys Ala Arg
            20                  25                  30

<210> SEQ ID NO 14
<211> LENGTH: 8
<212> TYPE: PRT
<213> ORGANISM: Mus Musculus

<400> SEQUENCE: 14

Glu Gly His Tyr Ala Leu Asp Tyr
1               5

<210> SEQ ID NO 15
<211> LENGTH: 11
<212> TYPE: PRT
<213> ORGANISM: Mus Musculus

<400> SEQUENCE: 15

Cys Gly Gln Gly Thr Ser Val Thr Val Ser Ser
1               5                   10

<210> SEQ ID NO 16
<211> LENGTH: 136
<212> TYPE: PRT
<213> ORGANISM: Mus Musculus

<400> SEQUENCE: 16

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Ser Gly Gly Ser Leu Lys Leu Ser Cys Ala Ala Ser Gly Phe Ile Phe
        35                  40                  45

Ser Ser Phe Gly Met Ser Trp Val Arg Gln Thr Pro Asp Lys Arg Leu
    50                  55                  60

Glu Trp Val Ala Thr Ile Ser Ser Gly Gly Arg Asn Ile Tyr Tyr Leu
65                  70                  75                  80

Asp Ser Val Lys Gly Arg Phe Thr Ile Ser Arg Asp Asn Val Lys Asn
                85                  90                  95

Ile Leu Tyr Leu Gln Met Ser Gly Leu Lys Ser Glu Asp Ser Ala Met
            100                 105                 110

Tyr Tyr Cys Ala Arg Glu Gly His Tyr Ala Leu Asp Tyr Cys Gly Gln
            115                 120                 125

Gly Thr Ser Val Thr Val Ser Ser
        130                 135

<210> SEQ ID NO 17
<211> LENGTH: 399
<212> TYPE: DNA
<213> ORGANISM: Mus Musculus

<400> SEQUENCE: 17
atggaatcac agacccaggt cctcatgttt cttctgctct gggtatctgg tgcctgtgca      60
gacattgtga tgacacagtc tccatcctcc ctggctacgt cagtaggaca gagggtcact     120
atgagctgca agtccagtca gaacctttta tatagtaccg atcaaaagaa ctatttggcc     180
tggttccagc agaaaccagg acagtctcct aaacttctac tatactttgc atccattagg     240
gaatctgggg tccctgatcg cttcataggc agtggatctg ggacagattt cactcttacc     300
atcagcagtg tgcaggctga agacctggca gattacttct gtcagcagca ttataacact     360
cctccgacgt tcggtggagg caccagactg gaaatcaaa                            399

<210> SEQ ID NO 18
<211> LENGTH: 408
<212> TYPE: DNA
<213> ORGANISM: Mus Musculus

<400> SEQUENCE: 18
atgaacttcg ggctcagctt gattttcctt gccctcattt taaaaggtgt ccagtgtgag      60
gtgcagctgg tggagtctgg gggagactta gtgaagtctg agggtccct gaaactctcc     120 tgtgccgcct ctggattcat tttcagtagc tttggcatgt cttgggttcg ccagactcca     180
gacaagaggc tggagtgggt cgcaaccatt agtagtggtg aaggaatat ctactattta     240 gacagtgtga aggggcgatt caccatctcc agagacaatg tcaagaacat cctgtacctg     300
caaatgagcg gtctgaagtc tgaggactca gccatgtact actgtgcaag agaggggcac     360
tatgctttgg actactgtgg tcaaggaact tcagtcaccg tctcctca                  408

<210> SEQ ID NO 19
<211> LENGTH: 133
<212> TYPE: PRT
<213> ORGANISM: Mus Musculus

<400> SEQUENCE: 19

Met Glu Ser Gln Thr Gln Val Leu Met Phe Leu Leu Leu Trp Val Ser
1               5                  10                  15

Gly Ala Cys Ala Asp Ile Val Met Thr Gln Ser Pro Ser Ser Leu Ala
            20                  25                  30

Thr Ser Val Gly Gln Arg Val Thr Met Ser Cys Lys Ser Ser Gln Asn
        35                  40                  45

Leu Leu Tyr Ser Thr Asp Gln Lys Asn Tyr Leu Ala Trp Phe Gln Gln
    50                  55                  60

Lys Pro Gly Gln Ser Pro Lys Leu Leu Leu Tyr Phe Ala Ser Ile Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Asp Tyr
            100                 105                 110

```
Phe Cys Gln Gln His Tyr Asn Thr Pro Pro Thr Phe Gly Gly Gly Thr
            115                 120                 125

Arg Leu Glu Ile Lys
        130

<210> SEQ ID NO 20
<211> LENGTH: 136
<212> TYPE: PRT
<213> ORGANISM: Mus Musculus

<400> SEQUENCE: 20

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Ser Gly Gly Ser Leu Lys Leu Ser Cys Ala Ala Ser Gly Phe Ile Phe
        35                  40                  45

Ser Ser Phe Gly Met Ser Trp Val Arg Gln Thr Pro Asp Lys Arg Leu
    50                  55                  60

Glu Trp Val Ala Thr Ile Ser Ser Gly Gly Arg Asn Ile Tyr Tyr Leu
65                  70                  75                  80

Asp Ser Val Lys Gly Arg Phe Thr Ile Ser Arg Asp Asn Val Lys Asn
                85                  90                  95

Ile Leu Tyr Leu Gln Met Ser Gly Leu Lys Ser Glu Asp Ser Ala Met
            100                 105                 110

Tyr Tyr Cys Ala Arg Glu Gly His Tyr Ala Leu Asp Tyr Cys Gly Gln
        115                 120                 125

Gly Thr Ser Val Thr Val Ser Ser
    130                 135

<210> SEQ ID NO 21
<211> LENGTH: 290
<212> TYPE: PRT
<213> ORGANISM: Homo sapiens

<400> SEQUENCE: 21

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160
```

```
Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 22
<211> LENGTH: 253
<212> TYPE: PRT
<213> ORGANISM: Homo sapiens

<400> SEQUENCE: 22

Phe Thr Val Thr Val Pro Lys Glu Leu Tyr Ile Ile Glu His Gly Ser
1               5                   10                  15

Asn Val Thr Leu Glu Cys Asn Phe Asp Thr Gly Ser His Val Asn Leu
            20                  25                  30

Gly Ala Ile Thr Ala Ser Leu Gln Lys Val Glu Asn Asp Thr Ser Pro
        35                  40                  45

His Arg Glu Arg Ala Thr Leu Leu Glu Glu Gln Leu Pro Leu Gly Lys
    50                  55                  60

Ala Ser Phe His Ile Pro Gln Val Gln Val Arg Asp Glu Gly Gln Tyr
65                  70                  75                  80

Gln Cys Ile Ile Ile Tyr Gly Val Ala Trp Asp Tyr Lys Tyr Leu Thr
                85                  90                  95

Leu Lys Val Lys Ala Ser Tyr Arg Lys Ile Asn Thr His Ile Leu Lys
            100                 105                 110

Val Pro Glu Thr Asp Glu Val Glu Leu Thr Cys Gln Ala Thr Gly Tyr
        115                 120                 125

Pro Leu Ala Glu Val Ser Trp Pro Asn Val Ser Val Pro Ala Asn Thr
    130                 135                 140

Ser His Ser Arg Thr Pro Glu Gly Leu Tyr Gln Val Thr Ser Val Leu
145                 150                 155                 160

Arg Leu Lys Pro Pro Pro Gly Arg Asn Phe Ser Cys Val Phe Trp Asn
                165                 170                 175

Thr His Val Arg Glu Leu Thr Leu Ala Ser Ile Asp Leu Gln Ser Gln
            180                 185                 190

Met Glu Pro Arg Thr His Pro Thr Trp Leu Leu His Ile Phe Ile Pro
        195                 200                 205

Phe Cys Ile Ile Ala Phe Ile Phe Ile Ala Thr Val Ile Ala Leu Arg
    210                 215                 220
```

```
Lys Gln Leu Cys Gln Lys Leu Tyr Ser Ser Lys Asp Thr Thr Lys Arg
225                 230                 235                 240

Pro Val Thr Thr Thr Lys Arg Glu Val Asn Ser Ala Ile
                245                 250
```

ANTIBODY THAT BINDS TO HUMAN PROGRAMMED DEATH LIGAND 2 (PD-L2) AND USES THEREOF

CROSS-REFERENCE TO RELATED APPLICATIONS

This application is a § 371 National Stage Application of PCT/US2016/052569, international filing date of Sep. 20, 2016, which claims the benefit of U.S. Provisional Application No. 62/221,472, filed Sep. 21, 2015, the contents of which are hereby incorporated by reference in their entirety.

FIELD OF THE INVENTION

The present invention relates to antibodies and antigen binding fragments thereof that bind to human Programmed Death Ligand 2 (PD-L2) and are useful for detecting PD-L2 expression in human tissue samples by immunohistochemical (IHC) analysis. The invention also relates to immunohistochemical (IHC) assays that employ this anti-human-PD-L2 antibody.

REFERENCE TO SEQUENCE LISTING SUBMITTED ELECTRONICALLY

The sequence listing of the present application is submitted electronically via EFS-Web as an ASCII formatted sequence listing with a file name "24188USPCT-SEQLIST-19MARCH2018.TXT", creation date of Mar. 19, 2018, and a size of 13.7 KB. This sequence listing submitted via EFS-Web is part of the specification and is herein incorporated by reference in its entirety.

BACKGROUND OF THE INVENTION

Immune checkpoint therapies targeting the programmed cell death protein 1 (PD-1) axis have resulted in groundbreaking improvements in clinical response in multiple human cancers (Brahmer et al., N Engl J Med 2012, 366: 2455-65: Garon et al. N Engl J Med 2015, 372: 2018-28: Hamid et al., N Engl J Med 2013, 369: 134-44; Robert et al., Lancet 2014, 384: 1109-17: Robert et al., N Engl J Med 2015, 372: 2521-32; Robert et al., N Engl J Med 2015, 372: 320-30; Topalian et al., N Engl J Med 2012, 366: 2443-54; Topalian et al., J Clin Oncol 2014, 32: 1020-30; Wolchok et al., N Engl J Med 2013, 369: 122-33). The interaction of the PD-1 receptor on T-cells with its ligands, PD-L1 and PD-L2, on tumor and immune infiltrating cells regulates T-cell mediated immune responses and may play a role in immune escape by human tumors (Pardoll D M. Nat Rev Cancer 2012, 12: 252-64). Binding of PD-1 to either of its ligands results in delivery of an inhibitory stimulus to the T cell. Immune therapies targeting the PD-1 axis include monoclonal antibodies directed to the PD-1 receptor (OPDIVO (nivolumab), Bristol-Myers Squibb, Princeton, N.J. and KEYTRUDA (pembrolizumab), Merck and Co., Inc. Kenilworth, N.J.) and also those that bind to the PD-L1 ligand (MPDL3280A; TECENTRIQ (atezolizumab), Genentech, San Francisco, Calif.). Both therapeutic approaches have demonstrated anti-tumor effects in several cancer types.

PD-L2 protein expression has been detected in the tumor microenvironment and on antigen presenting cells under certain conditions. Also, northern blot analysis of various tissues indicates that PD-L2 RNA is expressed in heart, placenta, liver, pancreas, spleen, lymph node, lung, smooth muscle and thymus. Thus, the ability to detect PD-L2 protein in situ in human tissues (e.g., by IHC assay) is important for investigating the biological activity of PD-L2, as well as for evaluating the anti-tumor efficacy of drugs targeting the PD-1 axis.

IHC assay is one of the most common techniques to detect a protein of interest in human tissue samples. Tumor tissue samples removed from a human patient are typically preserved for subsequent analysis by freezing individual tissue sections or by preparing formalin-fixed paraffin-embedded (FFPE) tissue sections. A need exists for anti-human PD-L2 antibodies that are capable of producing staining patterns for both frozen and FFPE tissue sections that have similar specificity and sensitivity, and to do so in a reproducible manner.

SUMMARY OF THE INVENTION

The present invention relates to a novel anti-human PD-L2 monoclonal antibody (mAb) that is capable of binding to PD-L2 protein in both frozen and FFPE human tissue sections in a highly specific, sensitive and reproducible manner. The present inventors believe that this novel antihuman PD-L2 mAb is superior to several commercially available anti-human PD-L2 antibodies for use in IHC assays based on one or more of the following criteria: specificity, sensitivity and reproducibility. The commercial anti-human PD-L2 antibodies that failed to satisfy all three of these three criteria are Clone #176611, a mouse IgG2b mAb available as Cat. No. MAB1224 from R&D Systems (Minneapolis, Minn. USA); R&D Systems Cat No. AF1224, a polyclonal goat IgG and Clone MIH18, a mouse IgG1 mAb available as Cat. No. 345501 from BioLegend® (San Diego, Calif. USA). Thus, the invention also relates to use of the anti-PD-L2 mAb of the present invention in the detection of PD-L2 expression on the surface of human cells, including in IHC assays to detect PD-L2 in FFPE tissue sections.

In one aspect, the invention provides an isolated monoclonal antibody (mAb), or an antigen binding fragment thereof, that specifically binds to human PD-L2. The isolated mAb, or antigen binding fragment thereof, comprises three light chain CDRs of CDRL1, CDRL2 and CDRL3 and three heavy chain CDRs of CDRH1, CDRH2 and CDRH3.

In one embodiment of the invention, CDRL1 is SEQ ID NO:2 or a variant of SEQ ID NO:2, CDRL2 is SEQ ID NO:4 or a variant of SEQ ID NO:4, and CDRL3 is SEQ ID NO:6 or a variant of SEQ ID NO:6.

In one embodiment. CDRH1 is SEQ ID NO:10 or a variant of SEQ ID NO:10, CDRH2 is SEQ ID NO: 12 or a variant of SEQ ID NO:12, and CDRH3 is SEQ ID NO:14 or a variant of SEQ ID NO:14.

In one embodiment, the three light chain CDRs are SEQ ID NO:2, SEQ ID NO:4, and SEQ ID NO:6 and the three heavy chain CDRs are SEQ ID NO: 10, SEQ ID NO: 12 and SEQ ID NO:14.

Some antibody and antigen binding fragments of the invention comprise a light chain variable region and a heavy chain variable region. In some embodiments, the light chain variable region comprises SEQ ID NO:8 or a variant of SEQ ID NO:8, and the heavy chain variable region comprises SEQ ID NO: 16 or a variant of SEQ ID NO: 16. In such embodiments, a variant light chain or heavy chain variable region sequence is identical to the reference sequence except having one, two, three, four or five amino acid substitutions in the framework (i.e., outside of the CDRs). In some embodiments, one, two, three, four or five of the amino acid substitutions are conservative substitutions.

In one antibody or antigen binding fragment of the invention, the light chain variable region is SEQ ID NO:8 and the heavy chain variable region is SEQ ID NO: 16.

In all of the above antibody embodiments, the isolated antibody may be a full-length antibody of any class of immunoglobulin, including IgM, IgG, IgD, IgA, and IgE. Preferably, the antibody is an IgG antibody, such as $IgG_1$, $IgG_2$, $IgG_3$, or $IgG_4$. In one embodiment, the antibody comprises two identical heavy chains and two identical light chains, wherein each heavy chain comprises a mouse $IgG_1$ constant region and each light chain comprises a mouse kappa constant region.

The invention also provides an antibody composition, which comprises any of the above-described antibodies or antibody fragments in a formulation. One suitable formulation comprises 20 mM sodium acetate and 9% sucrose at pH 5.0.

In any of the above embodiments, the antigen binding fragment may be a Fab fragment, a Fab' fragment, a $(Fab')_2$ fragment, an Fv fragment or an scFv fragment.

In any of the above embodiments, the antibody or antigen binding fragment may further comprise a detectable label.

The invention also provides isolated nucleic acid molecules encoding any of the antibody variable regions disclosed above. The invention also provides an expression vector comprising a sequence of nucleotides that encodes any of the antibodies or antigen binding fragments of the invention. In one embodiment, the nucleic acid molecule comprises a sequence of nucleotides as set forth in SEQ ID NO: 17 or SEQ ID NO: 18. In a further embodiment, the nucleic acid molecule comprises a sequence of nucleotides as set forth in SEQ ID NO: 17 and SEQ ID NO:18.

The invention also relates to a host cell comprising an expression vector that encodes any of the antibodies, antigen binding fragments, or antibody variable regions disclosed above. In one embodiment, the expression vector encodes both the heavy and light chains. In one embodiment, the expression vector comprises one or both of SEQ ID NO: 17 and SEQ ID NO:18.

The invention also provides a method of assaying a human tissue sample that has been removed from a human for PD-L2 expression. The method comprises contacting the tissue sample with a PD-L2 binding reagent under conditions that allow specific binding of the PD-L2 binding reagent to human PD-L2, removing unbound PD-L2 binding reagent, and detecting the presence or absence of bound PD-L2 binding agent. In one embodiment, the method further comprises quantifying the amount of bound binding reagent. The PD-L2 binding reagent is any of the monoclonal antibody or antigen binding fragments described above. In an embodiment, the PD-L2 binding reagent is an antibody which comprises SEQ ID NO:8 and SEQ ID NO: 16. In an embodiment, the tissue sample is from a tumor. In an embodiment, the tissue sample comprises tumor tissue removed from a patient diagnosed with bladder cancer, gastric cancer, head and neck squamous cell cancer (HNSCC), Hodgkin Lymphoma, melanoma, non-small cell lung cancer (NSCLC), renal cell cancer (RCC) or triple negative breast cancer (TNBC). In an embodiment, the method further comprises testing the tissue sample for PD-L1 expression. In an embodiment, another tissue sample removed from the patient has previously tested negative for PD-L2 expression.

In another aspect, the method comprises treating a patient diagnosed with a cancer. The method comprises determining if the patient tests positive by an IHC assay for PD-L2 expression using any of the anti-PD-L2 monoclonal antibody or antigen binding fragments described above, then the patient is treated with a PD-1 antagonist and if the patient tests negative for PD-L2 expression by the IHC assay, then the patient is not treated with a PD-1 antagonist. In an embodiment, the PD-1 antagonist is pembrolizumab.

In yet another aspect, the invention provides a kit for assaying a human tissue sample for PD-L2 expression. The kit comprises a PD-L2 binding agent and a set of reagents for detecting a complex comprising the binding agent bound to human PD-L2. The PD-L2 binding agent is any monoclonal antibody or antigen binding fragment described above that specifically binds to human PD-L2. In an embodiment, the PD-L2 binding reagent comprises SEQ ID NO:8 and SEQ ID NO:16.

BRIEF DESCRIPTION OF THE DRAWINGS

FIG. 1 shows the nucleotide sequences for antibody variable light and heavy chain cDNA (SEQ ID NO: 17 and SEQ ID NO: 18, respectively) prepared from total RNA isolated from hybridoma MEB123.3G2 and the predicted amino acid sequences encoded thereby (SEQ ID NO: 19 and SEQ ID NO:20, respectively), with brackets indicating nucleotide and amino acid sequences for the leader peptide and underlining indicating the nucleotide and amino acid sequences for the CDRs.

FIG. 6 shows the baseline characteristics of patients in HNSCC cohort (All-patients-as-treated population, see EXAMPLE 5).

FIG. 7 shows PDL-1 and PDL-2 status and overall clinical response (see EXAMPLE 5)

DETAILED DESCRIPTION OF THE INVENTION

Figure 2:
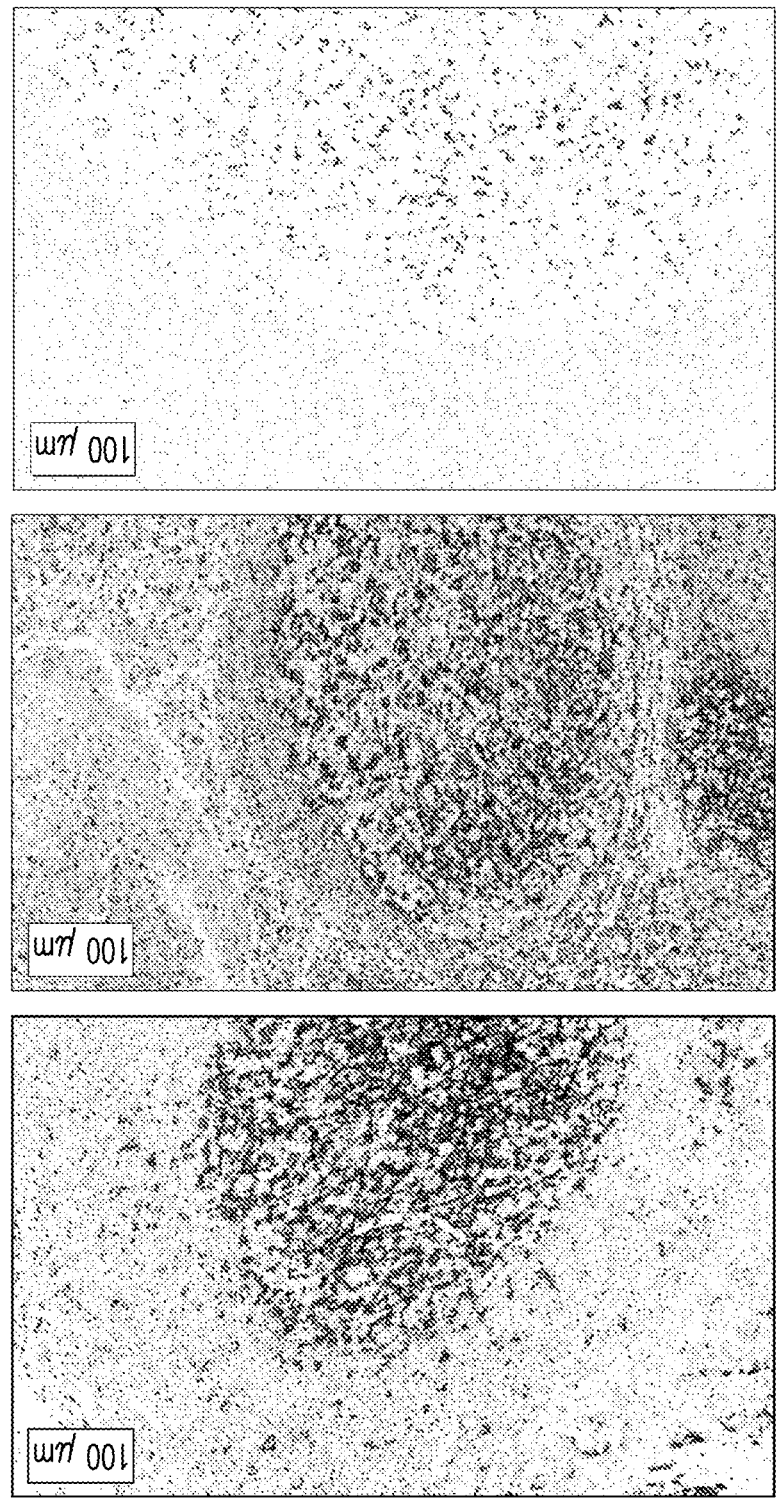
FIG. 2 shows FFPE tissue sections of normal human tonsil tissue stained with one of three anti-human PD-L2 antibodies: a monoclonal antibody of the invention (Clone 3G2, left panel) a commercially polyclonal antibody (AF1224, middle panel) and a monoclonal antibody (Clone MIH18, right panel).

Tumor-associated PD-L1 expression is related to clinical response to anti-PD-1 therapies; however, PD-L1-negative patients may also respond to anti-PD-1 therapies suggesting that other PD-1 interactions may be relevant to responsiveness. The prevalence and distribution of PD-L2, the other known ligand of PD-1 is not well-studied. Commercially available anti-human PD-L2 antibodies are unsatisfactory for detecting human PD-L2 in IHC assays of FFPE tissue sections. To this end, the present invention provides isolated anti-PD-L2 antigen binding proteins and methods of use of the antigen binding proteins in methods for the detection of PD-L2 expression in a human tissue sample. The invention further provides methods of using the PD-L2 antibodies of the invention, or antigen binding fragments thereof, to predict clinical responsiveness to anti-PD-1 treatment in patients in need of such treatment. In some embodiments, the patients have head and neck squamous cell carcinoma (HNSCC).

The clinical response to anti-PD-1 targeted therapies can vary in different tumor types and much effort has been directed toward finding predictive biomarkers to help identify patients who will derive most benefit from these therapies. Screening of patients eligible for PD-1 axis-targeted treatments has primarily focused on the evaluation of PD-L1 expression in tumors, as detected by immunohistochemistry (IHC). Although testing for PD-L1 expression has allowed for enrichment of responder populations in some tumor types, subsets of PD-L1 positive patients have responded poorly to anti-PD-1 axis therapies, and some PD-L1 negative patients have shown favorable responses (Garon et al., 2015, supra, Robert et al, 2015, supra, Herbst et al. *Nature* 2014, 515: 563-7: Tumeh et al., *Nature* 2014, 515: 568-71.). This suggests that molecular interactions with PD-1 other than PD-L1, including PD-L2, may be relevant towards predicting clinical responsiveness to these treatments.

The expression of PD-L2 in tumor tissue and its correlation with response to PD-1 axis-targeted therapy is not well-studied. Similar to PD-L1, PD-1 interaction with PD-L2 inhibits T cell proliferation, cytokine production, and T-cell cytolysis (Latchman et al., *Nat Immunol* 2001, 2: 261-8; Rodig et al., *Eur J Immunol* 2003, 33: 3117-26). Previous studies have found PD-L to be expressed in T and B cells, dendritic cells and macrophages as well as non-immune cells, while PD-L2 expression has been identified as more restricted to antigen-presenting cells, although inducible in other immune and non-immune cells by various microenvironmental stimuli (Latchman et al., 2001, supra, Lesterhuis et al., *Mol Immunol* 2011, 49: 1-3; Lesterhuis et al., *J Clin Invest* 2011, 121: 3100-8: Messal et al., *Mol Immunol* 2011, 48: 2214-9). These differences may reflect distinct functions for these 2 ligands within the PD-1 axis, wherein PD-L1 mediates a more generalized anti-inflammatory effect and PD-L2 may play a role in T-cell priming (Cheah et al., *Curr Opin Oncol* 2015, 27: 384-91). In limited studies PD-L2 expression has been demonstrated in human tumors from several indications examined, with expression detected in the absence of PD-L1 in some samples, and varied results regarding its relationship with clinical response (Herbst et al., 2014, supra, Taube et al., *Clin Cancer Res* 2014, 20: 5064-74: Schimd et al., *Journal of Clinical Oncology* 2016, 34 Suppl 15, 11506.).

Given that expression of PD-L2 either alone or in combination with PD-L1 could impact the efficacy of therapies targeting the PD-1 axis, the inventors herein assessed the prevalence and distribution of PD-L2 in more than 400 archival human tumor samples across 7 cancer indications using a novel PD-L2 IHC assay, which utilizes a PD-L2 antibody of the invention. PD-L2 expression was observed in all tumor types, and was expressed in stromal, tumor and endothelial cells. The inventors further show herein that the prevalence and distribution of PD-L2 correlated significantly with PD-L1 (P=0.0012-<0.0001); however, PD-L2 was detected in the absence of PD-L in some tumor types.

It is also shown that both PD-L1 and PD-L2 positivity significantly predicted clinical response to pembrolizumab, with the impact of PD-L2 status significant regardless of PD-L1 status. Overall response was greater in patients positive for both PD-L1 and PD-L2 (27.5%) than those positive only for PD-L1 (11.4%). PD-L2 status was also a significant predictor of progression-free survival (PFS) with pembrolizumab therapy irrespective of PD-L1 status. Longer median survival times for PFS and overall survival were observed for PD-L2-positive than PD-L2-negative patients.

Definitions and Abbreviations.

Throughout the detailed description and examples of the invention the following abbreviations will be used:
CDR Complementarity determining region in the immunoglobulin variable regions, defined using the Kabat numbering system, unless otherwise indicated
CHO Chinese hamster ovary
EC50 concentration resulting in 50% efficacy or binding
ELISA Enzyme-linked immunosorbant assay
FFPE formalin-fixed, paraffin-embedded
FR Framework region
HRP Horseradish peroxidase
HNSCC Head and neck squamous cell carcinoma
IC50 concentration resulting in 50% inhibition
IgG Immunoglobulin G
IHC Immunohistochemistry or immunohistochemical
mAb or Mab Monoclonal antibody
MES 2-(N-morpholino)ethanesulfonic acid
NCBI National Center for Biotechnology Information
NSCLC Non-small cell lung cancer
PCR Polymerase chain reaction
PD-1 Programmed Death 1
PD-L1 Programmed Cell Death 1 Ligand 1
PD-L2 Programmed Cell Death 1 Ligand 2
TNBC Triple negative breast cancer
$V_H$ Immunoglobulin heavy chain variable region
VK Immunoglobulin kappa light chain variable region
$V_L$ Immunoglobulin heavy chain variable region So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise.

"Activity" of a molecule may describe or refer to the binding of the molecule to a ligand or to a receptor, to catalytic activity: to the ability to stimulate gene expression or cell signaling, differentiation, or maturation: to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

Typically, an antibody or antigen binding fragment of the invention retains at least 10% of its human PD-L2 binding activity (when compared to the parental antibody, i.e., a tetrameric antibody comprising the light chain and heavy chain variable regions of antibody 3G2) when that activity is expressed on a molar basis. Preferably, an antibody or antigen binding fragment of the invention retains at least 20%, 50%, 70%, 80%, 90%, 95% or 100% or more of the human PD-L2 binding affinity as the parental antibody. It is also intended that an antibody or antigen binding fragment of the invention can include conservative or non-conservative amino acid substitutions (referred to as "conservative variants" or "function conserved variants" of the antibody) that do not substantially alter its biologic activity.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, and chimeric antibodies. "Parental antibodies" are antibodies obtained by exposure of an immune system to an antigen prior to modification of the antibodies for an intended use, such as humanization of an antibody for use as a human therapeutic antibody.

In some embodiments, the antibody comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The variable regions of each light/heavy chain pair form the antibody binding site. Thus, in general, an intact antibody has two binding sites. Except in bifunctional or bispecific antibodies, the two binding sites are, in general, the same.

Typically, the variable region of each of the heavy and light chains comprise three hypervariable regions, also called complementarity determining regions (CDRs), which are surrounded by relatively conserved framework regions (FR). In general, from N-terminal to C-terminal, the light chain and the heavy chain variable regions comprise FR1, CDR1, FR2, CDR2, FR3, CDR3 and FR4. Unless otherwise indicated, the assignment of amino acids to different regions of an antibody of the invention is in accordance with the definitions of Kabat (see, e.g., Kabat et al. (1991) Sequences of Proteins of Immunological Interest, 5th Ed. Public Health Service, National Institutes of Health, Bethesda, Md.; Kabat (1978) Adv. Prot. Chem. 32:1-75; Kabat, et al., (1977) J. Biol. Chem. 252:6609-6616). An alternative approach for assignment of CDRs employs the Chothia definitions (see, e.g., Chothia and Lesk (1987), J. Mol. Biol. 196: 901-917; Chothia, et al., (1989) Nature 342:878-883).

An antibody that "specifically binds to" a specified target protein is an antibody that exhibits preferential binding to the target protein as compared to other proteins, but this specificity does not require absolute binding specificity. Thus, an anti-PD-L2 antibody is specific for a human PD-L2 polypeptide comprising a given amino acid sequence, e.g., the amino acid sequence of a mature human PD-L2 molecule or the amino acid sequence of the extracellular domain of a mature human PD-L2 protein, if it binds to polypeptides comprising that sequence but does not bind to proteins lacking that sequence. An anti-hPD-L2 antibody, or antigen binding fragment thereof, is also considered "specific" for human PD-L2 if its binding is determinative of the presence of human PD-L2 in a sample, e.g. without producing undesired results such as false positives in an IHC diagnostic assay. The degree of specificity necessary for an anti-hPD-L2 antibody or antigen binding fragment may depend on the intended use of the antibody or fragment, and at any rate is defined by its suitability for use for an intended purpose. Antibodies, or binding fragments thereof, useful in the present invention will bind to human PD-L2 with an affinity that is at least two fold greater, preferably at least ten times greater, more preferably at least 20-times greater, and most preferably at least 100-times greater than the affinity with non-target proteins.

As used herein, unless otherwise indicated. "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments: diabodies: linear antibodies; single-chain antibody molecules, e.g., sc-Fv and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H$a and $C_H2$ domains, such that an interchain disulfide bond is formed between the two heavy chains. A F(ab') 2 fragment thus is composed of two Fab' fragments that are held together by a disulfide bond between the two heavy chains. An "F(ab')$_2$ fragment" can be the product of pepsin cleavage of an antibody.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "diabodies" refers to small antibody fragments with two antigen-binding sites, which fragments comprise a heavy chain variable domain (Vii) connected to a light chain variable domain ($V_L$) in the same polypeptide chain ($V_H$—$V_L$ or $V_L$—$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

"Framework region" or "FR" as used herein means an amino acid sequence in an antibody variable region that does not overlap with a CDR amino acid sequence.

Antibody 3G2 is the mouse anti-human PD-L2 mAb produced by hybridoma clone MEB123.3G2.038 and which comprises the structural features set forth in Table 1 below.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art

TABLE 1

Structural Features of Anti-human PD-L2 mAb 3G2

| Antibody Feature | Amino Acid Sequence | SEQ ID NO |
|---|---|---|
| Light Chain | | |
| Framework Region 1 | DIVMTQSPSSLATSVGQRVTMSC | 1 |
| CDRL1 | KSSQNLLYSTDQKNYLA | 2 |
| Framework Region 2 | WFQQKPGQSPKLLLY | 3 |
| CDRL2 | FASIRES | 4 |
| Framework Region 3 | GVPDRFIGSGSGTDFTLTISSVQAEDLADYFCC | 5 |
| CDRL3 | QQHYNTPPT | 6 |
| Framework Region 4 | FGGGTRLEIK | 7 |
| Variable Region | DIVMTQSPSSLATSVGQRVTMSCKSSQNLLYSTDQKNYLAWFQQKPGQSPKLLLYFASIRESGVPDRFIGSGSGTDFTLTISSVQAEDLADYFCQQHYNTPPTFGGGTRLEIK | 8 |
| Heavy Chain | | |
| Framework Region 1 | EVQLVESGGDLVKSGGSLKLSCAASGFIFS | 9 |
| CDRH1 | SFGMS | 10 |
| Framework Region 2 | WVRQTPDKRLEWVA | 11 |
| CDRH2 | TISSGGRNIYYLDSVKG | 12 |
| Framework Region 3 | RFTISRDNVKNILYLQMSGLKSEDSAMYYCAR | 13 |
| CDRH3 | EGHYALDY | 14 |
| Framework Region 4 | CGQGTSVTVSS | 15 |
| Variable Region | MNFGLSLIFLALILKGVQCEVQLVESGGDLVKSGGSLKLSCAASGFIFSSFGMSWVRQTPDKRLEWVATISSGGRNIYYLDSVKGRFTISRDNVKNILYLQMSGLKSEDSAMYYCAREGHYALDYCGQGTSVTVSS | 16 | recognize that, in general, single amino acid substitutions in non-essential regions of a polypeptide do not substantially alter biological activity (see. e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 2.

TABLE 2

Exemplary conservative amino acid substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, an anti-PD-L2 antibody that consists essentially of a recited amino acid sequence may also include one or more amino acids, including substitutions of one or more amino acid residues, which do not materially affect the binding specificity or activity.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide: a promoter or enhancer is operably linked to a coding sequence if it affects the transcription of the sequence: or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Diagnostic anti-PD-L monoclonal antibody" means a mAb which specifically binds to the mature form of the designated PD-L (PD-L1 or PDL2) that is expressed on the surface of certain mammalian cells.

As used herein, a diagnostic anti-human PD-L1 mAb or an anti-hPD-L1 mAb refers to a mAb that specifically binds to mature human PD-L. A mature human PD-L1 molecule consists of amino acids 19-290 of the following sequence:

```
                                    (SEQ ID NO: 21)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.
```

Specific examples of diagnostic anti-human PD-L1 mAbs useful as diagnostic mAbs for immunohistochemistry (IHC) detection of PD-L1 expression in formalin-fixed, paraffin-embedded (FFPE) tumor tissue sections are antibody 20C3 and antibody 22C3, which are described in the copending international patent application PCT/US13/075932, filed 18 Dec. 2013 and published as WO2014/100079 on 26 Jun. 2014. Another anti-human PD-L1 mAb that has been reported to be useful for IHC detection of PD-L1 expression in FFPE tissue sections (Chen, B. J. et al., *Clin Cancer Res* 19: 3462-3473 (2013)) is a rabbit anti-human PD-L1 mAb publicly available from Sino Biological, Inc. (Beijing, P.R. China; Catalog number 10084-R015).

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990)*J. Mol. Biol.* 215:403-410; Gish, W., et al., (1993) *Nature Genet.* 3:266-272; Madden, T. L., et al., (1996) *Meth. Enzymol* 266:131-141: Altschul, S. F., et al., (1997) *Nucleic Acids Res.* 25:3389-3402; Zhang, J., et al., (1997) *Genome Res.* 7:649-656; Wootton, J. C., et al., (1993) *Comput. Chem.* 17:149-163; Hancock. J. M. et al., (1994) *Comput. Appl. Biosci.* 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O.

Dayhoff (ed.), pp. 345-352. Natl. Biomed. Res. Found., Washington, D.C.: Schwartz, R. M., et al., "Matrices for detecting distant relationships." in *Atlas of Protein Sequence and Structure*. (1978) vol. 5, suppl. 3." M. O. Dayhoff (ed.), pp. 353-358, Natl. Biomed. Res. Found., Washington, D.C.; Altschul. S. F., (1991) *J. Mol. Biol.* 219:555-565: States. D. J., et al., (1991) *Methods* 3:66-70; Henikoff. S., et al., (1992) *Proc. Natl. Acad. Sci. USA* 89:10915-10919: Altschul, S. F., et al., (1993) *J. Mol. Evol.* 36:290-300; ALIGNMENT STATISTICS: Karlin, S., et al., (1990) *Proc. Nat. Acad. Sci. USA* 87:2264-2268; Karlin, S., et al., (1993) *Proc. Natl. Acad. Sci. USA* 90:5873-5877; Dembo, A., et al., (1994) *Ann. Prob.* 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

The terms "human PD-L2", "hPD-L2" and "human mature PD-L2" are used interchangeably herein, and shall be understood to mean the same molecule unless otherwise indicated or readily apparent from the context. A mature PD-L2 molecule lacks the presecretory leader sequence, also referred to as a leader peptide. Alternative names or synonyms for PD-L2 include PDCD1L2, PDL2, B7-DC, Btdc and CD273. A mature human PD-L2 amino acid sequence is described in NCBI Locus No.: NP_079515 and consists of a sequence of amino acids as shown below:

FTVTVPKELYIIEHGSNVTLECNFDTGSHVNLGAITASLQKVENDTSPHR

ERATLLEEQLPLGKASFHIPQVQVRDEGQYQCIIIYGVAWDYKYLTLKVK

ASYRKINTHILKVPETDEVELTCQATGYPLAEVSWPNVSVPANTSHSRTP

EGLYQVTSVLRLKPPPGRNFSCVFWNTHVRELTLASIDLQSQMEPRTHPT

WLLHIFIPFCIIAFIFIATVIALRKQLCQKLYSSKDTTKRPVTTTKREVN

SAI (SEQ ID NO:22). The extracellular domain of mature human PD-L2 consists of amino acids 1-220 of SEQ ID NO:22.

"Isolated antibody" or "isolated antibody fragment" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The term "monoclonal antibody", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see. e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

As used herein, "polymerase chain reaction" or "PCR" refers to a procedure or technique in which specific nucleic acid sequences, RNA and/or DNA, are amplified as described in, e.g., U.S. Pat. No. 4,683,195. Generally, sequence information from the ends of the region of interest or beyond is used to design oligonucleotide primers. These primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261

"PD-L1" or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and real-time quantitative RT-PCR.

"Tissue Section" refers to a single part or piece of a tissue sample, e.g., a thin slice of tissue cut from a sample of a normal tissue or of a tumor.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

Anti-PD-L2 Antibodies

The invention provides an isolated antibody, or antigen binding fragment thereof, that specifically binds to human PD-L2. The isolated antibody, or antigen binding fragment thereof, comprises three light chain CDRs (CDRL1, CDRL2 and CDRL3) and three heavy chain CDRs (CDRH1, CDRH2 and CDRH3). The isolated anti-PD-L2 antibodies or binding fragments thereof are useful for the detection of human PD-L2 expression on the surface of cells. Examples of anti-PD-L2 antibodies of the invention include, but are not limited to, antibodies that comprise the light and heavy chain amino acid sequences of antibody 3G2 (see Table 1, $V_L$ comprises, consists or consists essentially of SEQ ID NO:8 and $V_H$ comprises, consists or consists essentially of SEQ ID NO: 16).

In embodiments of the invention, the recombinant antigen binding protein that binds PD-L2 comprises three, four, five, or six of the CDRs of the antigen binding protein disclosed herein (Table 1). In one embodiment, the invention provides an isolated antibody, or antigen binding fragment thereof, that comprises all six of the CDR's of antibody 3G2.

In one embodiment of the invention, CDRL1 is SEQ ID NO:2 or a variant of SEQ ID NO:2, CDRL2 is SEQ ID NO:4 or a variant of SEQ ID NO:4, and CDRL3 is SEQ ID NO:6 or a variant of SEQ ID NO:6.

In antibodies and antigen binding fragments of the invention, a variant CDR sequence (light chain or heavy chain) is identical to the reference sequence with the exception of one or two amino acid substitutions relative to the reference sequence. In some embodiments, the amino acid substitutions are conservative amino acid substitutions. In one embodiment of the invention, the variant CDR has only one amino acid substitution in the reference CDR sequence. In one embodiment, the one amino acid substitution in the variant CDR is a conservative substitution. In preferred embodiments, at most two of the three light chain CDRs are a variant sequence, and at most two of the three heavy chain CDRs are a variant sequence. In more preferred embodiments, a variant sequence is present in only three, two or one of the six CDRs.

In one embodiment of the invention, the antigen binding protein comprises a $V_L$ domain comprising a CDRL1 of SEQ ID NO: 2, a CDRL2 of SEQ ID NO: 4 and a CDRL3 of SEQ ID NO: 6.

In a further embodiment, the antigen binding protein comprises a $V_H$ domain comprising a sequence of amino acids as set forth in SEQ ID NO:8. In one embodiment, the $V_H$ domain consists of SEQ ID NO:8.

The isolated antigen binding protein that binds PD-L2 can comprise at least one heavy chain variable ($V_H$) domain comprising one or more of CDRH1, CDRH2 and CDRH3 of the antigen binding protein of the invention, e.g. antibody 3G2. In specific embodiments, the antigen binding protein comprises a $V_H$ domain comprising three CDRs of an antigen binding protein of the invention.

In one embodiment, CDRH1 is SEQ ID NO:10 or a variant of SEQ ID NO:10, CDRH2 is SEQ ID NO: 12 or a variant of SEQ ID NO:12, and CDRH3 is SEQ ID NO:14 or a variant of SEQ ID NO:14.

In one embodiment, the antigen binding protein comprises a $V_H$ domain comprising the CDRH1 set forth in SEQ ID NO: 10, the CDRH2 set forth in SEQ ID NO: 12 and the CDRH3 set forth in SEQ ID NO: 14.

In a further embodiment, the antigen binding protein comprises a $V_H$ domain comprising a sequence of amino acids as set forth in SEQ ID NO: 16. In one embodiment, the $V_H$ domain consists of SEQ ID NO: 16.

In one embodiment of the invention, the antigen binding protein comprises a $V_L$ domain comprising an amino acid sequence as set forth in SEQ ID NO:8 and a $V_H$ domain comprising an amino acid sequence as set forth in SEQ ID NO: 16. In a further embodiment of the invention, the antigen binding protein comprises a $V_L$ domain consisting of an amino acid sequence as set forth in SEQ ID NO:8 and a $V_H$ domain consisting of an amino acid sequence as set forth in SEQ ID NO: 16.

In other embodiments, the invention provides antigen binding proteins that are derivatives of the antigen binding proteins disclosed herein. Antigen binding protein derivatives of the invention specifically bind PD-L2 and have $V_L$ domains and $V_H$ domains with at least 50%, 75%, 80%, 85%, 90%, 95%, 98% or 99% sequence identity with the $V_L$ domains and $V_H$ domains of the antibodies disclosed herein (e.g., in Tables 1) while still exhibiting the desired binding and functional properties (e.g., PD-L2 binding). In another embodiment the antigen binding protein derivatives of the present invention comprises $V_L$ and $V_H$ domains having up to 0, 1, 2, 3, 4, 5, 6, 7, 8, 9, 10 or more conservative or non-conservative amino acid substitutions, while still exhibiting the desired binding and functional properties.

Antigen binding protein derivatives of the invention also encompass those derivatives that specifically bind PD-L2 and have CDRs (i.e., CDRL1, CDRL2 and CDRL3) of a $V_L$ domain and CDRs of a $V_H$ domain with at least 50%, 75%, 80%, 85%, 90%, 95%, 98% or 99% sequence identity with the CDRs disclosed herein for the $V_L$ domains and $V_H$ domains of the antigen binding proteins of the invention (e.g., in Table 1) while still exhibiting the desired binding and functional properties (e.g., PD-L2 binding). In another embodiment the antigen binding protein derivative of the invention comprises CDRs of disclosed $V_L$ and $V_H$ domains having up to 0, 1, 2, 3 or more conservative or non-conservative amino acid substitutions, while still exhibiting the desired binding and functional properties.

Sequence identity refers to the degree to which the amino acids of two polypeptides are the same at equivalent positions when the two sequences are optimally aligned. Sequence identity can be determined using a BLAST algorithm wherein the parameters of the algorithm are selected to give the largest match between the respective sequences over the entire length of the respective reference sequences. The following references relate to BLAST algorithms often used for sequence analysis: BLAST ALGORITHMS: Altschul, S. F., et al., (1990) *J. Mol. Biol.* 215:403-410; Gish, W., et al., (1993) Nature Genet. 3:266-272; Madden, T. L., et al., (1996) Meth. Enzymol. 266:131-141; Altschul, S. F., et al., (1997) *Nucleic Acids Res.* 25:3389-3402; Zhang, J., et al., (1997) Genome Res. 7:649-656; Wootton, J. C., et al., (1993) Comput. Chem. 17:149-163: Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz. R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877: Dembo, A., et al., (1994) Ann. Prob. 22:2022-2039: and Altschul, S. F. "Evaluating the statistical significance of multiple distinct local alignments." in Theoretical and Computational Methods in Genome Research (S. Suhai, ed.), (1997) pp. 1-14, Plenum, New York.

Typically, an antigen binding protein derivative of the invention retains at least 10% of its PD-L2 binding activity (when compared to the parental antigen binding protein) when that activity is expressed on a molar basis. Preferably, an antigen binding protein derivative of the invention retains at least 20%, 50%, 70%, 80%, 90%, 95% or 100% of the PD-L2 binding affinity as the parental antigen binding protein.

The $V_H$ or $V_L$ chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

As used herein, the term "hypervariable region" refers to the amino acid residues of an antibody that are responsible for antigen binding. The hypervariable region comprises amino acid residues from the light chain variable region CDRs and the heavy chain variable region CDRs.

Function-conservative derivatives of the antigen binding proteins of the invention are also contemplated by the present invention. As used herein, the term "function-conservative derivative" refers to antigen binding proteins in which one or more amino acid residues have been changed without altering a desired property, such an antigen affinity and/or specificity and/or neutralizing activity. Such variants include, but are not limited to, replacement of an amino acid with one having similar properties, such as the conservative amino acid substitutions of Table 2.

Also provided are recombinant polypeptides comprising the $V_L$ domains of the anti-PD-L2 antigen binding protein of the invention and recombinant polypeptides comprising the $V_H$ domains of the anti-PD-L2 antigen binding protein of the invention having up to 1, 2, 3, 4, or 5 or more amino acid substitutions, while still exhibiting the ability to bind to PD-L2 with high affinity and specificity.

In another embodiment, provided is an antigen binding protein that has a $V_L$ domain and/or a $V_H$ domain with at least 95%, 90%, 85%, 80%, 75% or 50% sequence homology to the $V_L$ domain or $V_H$ domain described herein, and exhibits specific binding to PD-L2. In another embodiment the antigen binding protein of the present invention comprises $V_L$ and $V_H$ domains (with and without signal sequence) having up to 1, 2, 3, 4, or 5 or more amino acid substitutions, and exhibits specific binding to PD-L2.

In another embodiment, the invention includes an antibody or antigen binding fragment thereof that specifically binds human PD-L2 and has $V_L$ domains and $V_H$ domains and shares 100% sequence homology to the light and heavy chain CDRs of Table 1, and at least 90%, 92%, 94%, 96%, 98% or 99% sequence homology to the light and heavy chain mature variable regions of Table 1.

Immunoglobulins may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The invention comprises antibodies and antigen binding fragments of any of these classes or subclasses of antibodies.

Nucleic Acids

The present invention also provides recombinant nucleic acids encoding the immunoglobulin chains of anti-PD-L1 antibodies and antigen binding fragments disclosed herein. For example, the present invention includes nucleic acids encoding the amino acid sequences described in Table 1, as well as nucleic acids which hybridize thereto.

In one embodiment, the recombinant nucleic acid encodes an antigen binding protein comprising a light chain variable ($V_L$) domain comprising the CDRL1, CDRL2 and CDRL3 of the antigen binding protein disclosed herein (SEQ ID NOs: 2, 4, and 6).

In one embodiment, the recombinant nucleic acid encodes antigen binding protein comprising a heavy chain variable ($V_H$) domain comprising the CDRH1, CDRH2 and CDRH3 of the antigen binding protein disclosed herein (SEQ ID NOs: 10, 12, and 14).

In one embodiment, the recombinant nucleic acid encodes an antigen binding protein comprising at least one light chain variable ($V_L$) domain and at least one heavy chain variable ($V_H$) domain, wherein the $V_L$ domain comprises three CDRs having a sequence of amino acids as set forth in SEQ ID NO: 2, 4, and 6, and the $V_H$ domain comprises three CDRs having a sequence of amino acids as set forth in SEQ ID NOs:10, 12, and 14. In one embodiment, the isolated nucleic acid encodes the light chain variable region set forth in SEQ ID NO:8 and the heavy chain variable region set forth in SEQ ID NO: 16. In some embodiments the isolated nucleic acid encodes both a light chain and a heavy chain on a single nucleic acid molecule, and in other embodiments the light and heavy chains are encoded on separate nucleic acid molecules. In another embodiment the nucleic acids further encodes a signal sequence.

Also provided by the invention are nucleotide sequences for antibody variable light and heavy chain cDNA (SEQ ID NO: 17 and SEQ ID NO: 18, respectively) prepared from total RNA isolated from hybridoma MEB123.3G2

The present invention further comprises nucleic acids which hybridize to nucleic acids encoding the anti-PD-L2 antigen binding proteins disclosed herein. In general, the nucleic acids hybridize under moderate or high stringency conditions to nucleic acids that encode antigen binding proteins disclosed herein and also encode antigen binding proteins that maintain the ability to specifically bind to PD-L2. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., supra). The conditions of temperature and ionic strength determine the "stringency" of the hybridization. Typical low stringency hybridization conditions include 55° C. 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, e.g., oligonucleotides, the position of mismatches becomes more important, and the length of the oligonucleotide determines its specificity (see Sambrook, et al., supra, 11.7-11.8).

In another embodiment, the invention provides an isolated nucleic acid or nucleic acids, for example DNA, encoding at least one of the polypeptide chains of the isolated anti-PD-L2 antibodies or antigen binding fragments described herein. In some embodiments the isolated nucleic acid encodes both a light chain and a heavy chain on a single nucleic acid molecule, and in other embodiments the light and heavy chains are encoded on separate nucleic acid molecules. In another embodiment the nucleic acids further encodes a signal sequence.

Also included in the present invention are nucleic acid molecules comprising a sequence of nucleotides that encode the anti-PD-L2 antigen binding proteins derivatives described herein.

The present invention also provides expression vectors comprising the isolated nucleic acid molecules of the invention, wherein the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium, and isolating the antigen or antigen binding fragment thereof from the host cell or culture medium.

Epitope Binding

The present invention further provides antibodies or antigen binding fragments thereof that block binding of a tetrameric antibody that comprises the light and heavy chain amino acid sequences of antibody 3G2 (the "reference antibody") to human PD-L2 by binding to the same epitope as the reference antibody. Such antibodies and binding fragments may be identified using any cross-blocking or competition analysis known in the art. A first antibody is considered to cross-block binding of a second antibody if prebinding the target with the first antibody to saturation increases the concentration of second antibody needed to achieve half-maximal binding of the target by 2-, 3-, 4-, 5-, 10-, 20-, 50-, 100-, 200-fold or more. The binding epitope for a cross-blocking antibody can be identified using techniques well-known in the art.

One such epitope mapping technique is hydrogen/deuterium exchange coupled with proteolysis and mass spectrometry (HDX-MS). This method relies on the accurate measurement and comparison of the degree of deuterium incorporation by an antigen when incubated in heavy water ($D_2O$) on its own and in the presence of its antibody at various time intervals. Deuterium is exchanged with hydrogen on the amide backbone of the proteins in exposed areas whereas regions of the antigen bound to the antibody will be protected and will show less or no exchange after analysis by liquid chromatography-tandem mass spectrometry (LC-MS/MS) of proteolytic fragments.

Methods of Making Antibodies and Antigen Binding Fragments Thereof

Antibodies of the invention may be made by culturing a hybridoma clone that expresses the desired antibody. For example, about 1 gram of the 3G2 antibody may be produced and purified from the mouse hybridoma cell line MEB123.3G2.038 using the following procedure. Frozen MEB123.3G2.038 cells are thawed into a shake flask containing hybridoma serum free media with 2 mM additional L-glutamine with or without 0.18% Pluronic F-68. The presence of Pluronic F-68 may improve the viability of the shake flask culture. Once the cells are completely adapted into shake flask, a 20 liter production culture is performed in serum free media in a WAVE bioreactor (GE Healthcare Life Sciences) with the addition of 10% CHO CD efficient Feed B (Invitrogen, Catalogue # A 10240-01). For cell expansion, a 1 liter culture is initiated in a small WAVE bag, and then the 1 L WAVE culture is expanded into a 20 L culture in the WAVE bioreactor. The 20 liter culture may be initiated at a cell density of $0.5 \times 10^6$ viable cells/mL, fed with 10% CHO CD Efficient Feed B on Day 1, and pH adjusted daily with IN $Na_2CO_3$. The cells are harvested after four days. Small samples may be collected daily for NOVA analysis.

Anti-hPD-L2 antibodies of the invention may be purified from a hybridoma culture by the following process. The hybridoma culture is clarified by depth filtration using 1.2 micrometer glass fiber and 0.2 micrometer cellulose acetate filter. An equal volume of 2× ProSepA Buffer (100 mM Boric Acid, 5M NaCl, pH 8.5) is added to the clarified harvest and the diluted harvest is loaded onto a 170 mL bed volume Protein-A column. The column is washed with 5 column volumes (CV) of 1× ProSepA Buffer (50 mM Boric Acid, 2.5M NaCl, pH 8.5), then washed with 2 CV of 1×PBS, and the anti-hPD-L2 antibody eluted with 5 CV of Elution Buffer (0.1M Glycine, pH 3.0). The elution fractions containing IgG are combined and the pH neutralized by adding ¹⁄₁₀ th volume of 1.0 M Tris, pH buffer. The neutralized antibody composition is then sterile filtered using a 10 kDa disposable TFF cassette. The antibody may be formulated for storage by diafiltration against 10 liter of formulation buffer (20 mM sodium acetate, 9% sucrose. pH 5.0) and using 20 volume changes.

The anti-PD-L2 antibodies disclosed herein may also be produced recombinantly (e.g., in an *E. coli*/T7 expression system). In this embodiment, nucleic acids encoding the antibody molecules of the invention (e.g., $V_H$ or $V_L$) may be inserted into a pET-based plasmid and expressed in the *E. coli*/TF7 system. There are several methods by which to produce recombinant antibodies which are known in the art. One example of a method for recombinant production of antibodies is disclosed in U.S. Pat. No. 4,816,567. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040, 4,740,461 and 4,959,455.

Anti-PD-L2 antibodies can also be produced by any of the methods set forth in U.S. Pat. No. 6,331,415.

Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

The present invention further includes antibody fragments of the anti-PD-L2 antibodies disclosed herein. The antibody fragments include F(ab)$_2$ fragments, which may be produced by enzymatic cleavage of an IgG by, for example, pepsin.

In one embodiment, the antibody or antigen binding fragment comprises a heavy chain constant region, e.g. a human constant region, such as γ1, γ2, γ3, or γ4 human heavy chain constant region or a variant thereof. In another embodiment, the antibody or antigen binding fragment comprises a light chain constant region, e.g. a human light chain constant region, such as lambda or kappa human light chain region or variant thereof. By way of example, and not limitation the human heavy chain constant region can be γ1 and the human light chain constant region can be kappa. In an alternative embodiment, the Fc region of the antibody is γ4 with a Ser228Pro mutation (Schuurman, J et. al., *Mol. Immunol.* 38: 1-8, 2001).

Antibody Engineering

Further included are embodiments in which the anti-PD-L2 antigen binding proteins are engineered to include modifications to framework residues within the variable domains of a parental antigen binding proteins, e.g. to improve the properties of the antigen binding proteins. Typically such framework modifications are made to decrease the immunogenicity of the antigen binding protein. This is usually accomplished by replacing non-CDR residues in the variable domains (i.e. framework residues) in a parental antigen binding proteins with analogous residues from the immune repertoire of the species in which the antigen binding protein is to be used, e.g. human residues in the case of human therapeutics. Such an antibody is referred to as a "humanized" antigen binding protein. In some cases it is desirable to increase the affinity, or alter the specificity of an engineered (e.g. humanized) antigen binding protein. One approach is to "backmutate" one or more framework residues to the corresponding germline sequence. More specifically, an antigen binding protein that has undergone somatic mutation can contain framework residues that differ from the germline sequence from which the antigen binding protein is derived. Such residues can be identified by comparing the framework sequences to the germline sequences from which the antigen binding protein is derived. Another approach is to revert to the original parental residue at one or more positions of the engineered (e.g. humanized) antigen binding protein, e.g. to restore binding affinity that may have been lost in the process of replacing the framework residues. (See, e.g., U.S. Pat. Nos. 5,693,762, 5,585,089 and 5,530,101.)

In particular embodiments, it will be desirable to change certain amino acids containing exposed side-chains to another amino acid residue in order to provide for greater chemical stability of the final antigen binding protein as follows. The deamidation of asparagine may occur on N-G or D-G sequences and result in the creation of an isoaspartic acid residue that introduces a kink into the polypeptide chain and decreases its stability (isoaspartic acid effect). In certain embodiments, the antigen binding proteins of the present disclosure do not contain asparagine isomerism sites.

For example, an asparagine (Asn) residue may be changed to Gln or Ala to reduce the potential for formation of isoaspartate at any Asn-Gly sequences, particularly within a CDR. A similar problem may occur at an Asp-Gly sequence. Reissner and Aswad (2003) *Cell. Mol. Life Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.*

662:261. In addition, any methionine residues (typically solvent exposed Met) in CDRs may be changed to Lys, Leu, Ala. or Phe in order to reduce the possibility that the methionine sulfur would oxidize, which could reduce antigen binding affinity and also contribute to molecular heterogeneity in the final antibody preparation. Id. In one embodiment, the methionine is changed to alanine (Ala). Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for human PD-L2 to unacceptable levels.

TABLE 3

Exemplary stabilizing variants for CDRs

| CDR Residue | Stabilizing Variant Sequence |
|---|---|
| Asn-Gly | Gln-Gly, Ala-Gly, or Asn-Ala |
| (N-G) | (Q-G), (A-G), or (N-A) |
| Asp-Gly | Glu-Gly, Ala-Gly or Asp-Ala |
| (D-G) | (E-G), (A-G), or (D-A) |
| Met (typically solvent exposed) | Lys, Leu, Ala, or Phe |
| (M) | (K), (L), (A), or (F) |
| Asn | Gln or Ala |
| (N) | (Q) or (A) |
| Asn-Pro | Gln-Pro, Ala-Pro, or Asn-Ala |
| (N-P) | (Q-P), (A-P), or (N-A) |

The variations for the $V_H$ and/or $V_L$ CDRs can be independently selected in any combination. Additionally, any variation described herein can be independently selected in any combination, as long as the desired activity or binding ability is maintained.

Engineering of the Fc Region

The antigen binding proteins disclosed herein can also be engineered to include modifications within the Fc region, typically to alter one or more functional properties of the antigen binding protein, such as serum half-life, complement fixation, Fc receptor binding, and/or effector function (e.g., antigen-dependent cellular cytotoxicity). Furthermore, the antigen binding proteins disclosed herein can be chemically modified (e.g., one or more chemical moieties can be attached to the antigen binding protein) or be modified to alter its glycosylation, again to alter one or more functional properties of the antigen binding protein. Each of these embodiments is described in further detail below. The numbering of residues in the Fc region is that of the EU index of Kabat.

The antigen binding proteins disclosed herein also include antigen binding proteins with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antigen binding proteins, enabling less frequent dosing and thus increased convenience and decreased use of material. See Presta (2005) *J. Allergy Clin. Immunol.* 116: 731 at 734-35.

In one embodiment, the antigen binding protein is an antibody or fragment thereof of an IgG4 isotype antibody comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the antigen binding protein is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antigen binding protein can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antigen binding proteins. For example, one or more amino acids selected from amino acid residues 234, 235, 236, 237, 297, 318, 320 and 322 can be replaced with a different amino acid residue such that the antigen binding protein has an altered affinity for an effector ligand but retains the antigen binding ability of the parent antigen binding protein. The effector ligand to which affinity is altered can be, for example, an Fc receptor or the C component of complement. This approach is described in further detail in U.S. Pat. Nos. 5,624,821 and 5,648,260.

In another example, one or more amino acid residues within amino acid positions 231 and 239 are altered to thereby alter the ability of the antigen binding protein to fix complement. This approach is described further in PCT Publication WO 94/29351.

In yet another example, the Fc region is modified to increase or decrease the ability of the antigen binding proteins to mediate antibody dependent cellular cytotoxicity (ADCC) and/or to increase or decrease the affinity of the antigen binding proteins for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the antigen binding protein comprises a particular glycosylation pattern. For example, an aglycosylated antigen binding protein can be made (i.e., the antigen binding protein lacks glycosylation). The glycosylation pattern of an antigen binding protein may be altered to, for example, increase the affinity or avidity of the antigen binding protein for an antigen. Such modifications can be accomplished by, for example, altering one or more of the glycosylation sites within the antigen binding protein sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. Pat. Nos. 5,714,350 and 6,350,861.

Antibody Conjugates

The anti-PD-L2 antibodies and antibody fragments disclosed herein may also be conjugated to a chemical moiety such as a radionuclide or other detectable label. Radionuclides include $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{6}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and Fe. Fluorescent or chemilluminescent labels include fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibody molecules to the various moieties may be employed, including those methods described by Hunter, et al., (1962) *Nature* 144:945; David, et al., (1974) *Biochemistry* 13:1014; Pain, et al., (1981) J. Immunol. Meth. 40:219; and Nygren, J., (1982) *Histochem. and Cytochem.* 30:407. Methods for conjugating antibodies are conventional and very well known in the art.

Experimental and Diagnostic Uses

The anti-PD-L2 antibodies and antibody fragments disclosed herein may be used to specifically detect human PD-L2 expressed on the surface of a cell. The cell may be present in a tissue or serum sample obtained from a human individual and the detection of PD-L2 expression is performed using any of a variety of in vitro assay methods known in the art.

For example, particular embodiments include ELISA assays (enzyme-linked immunosorbent assay), which typically comprises the following steps:

(a) coat a substrate (e.g., surface of a microtiter plate well, e.g., a plastic plate) with an anti-PD-L1 antibody antigen-binding fragment thereof:

(b) apply a sample to be tested for the presence of human PD-L1 to the substrate:

(c) wash the plate, so that unbound material in the sample is removed;

(d) apply detectably labeled antibodies (e.g., enzyme-linked antibodies) which are also specific to human PD-L1;

(e) wash the substrate, so that the unbound, labeled antibodies are removed;

(f) if the labeled antibodies are enzyme linked, apply a chemical which is converted by the enzyme into a fluorescent signal; and (g) detect the presence of the labeled antibody.

In a further embodiment, the labeled antibody is labeled with peroxidase which reacts with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody is labeled with a detectable radioisotope (e.g., $^{3}$H) which can be detected by scintillation counter in the presence of a scintillant.

Anti-PD-L2 antibodies and antigen binding fragments thereof of the invention may be used in a Western blot or immunoprotein blot procedure. Such a procedure forms part of the present invention and includes e.g.:

(1) contacting a membrane or other solid substrate to be tested for the presence of human PD-L2 thereof with an antibody or antigen-binding fragment thereof of the invention. Such a membrane may take the form of a nitrocellulose or vinyl-based (e.g., polyvinylidene fluoride (PVDF)) membrane to which proteins to be tested for the presence of PD-L2 in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-PD-L2 antibody or fragment, the membrane is optionally blocked, e.g., with non-fat dry milk or the like so as to bind non-specific protein binding sites on the membrane.

(2) washing the membrane one or more times to remove unbound anti-PD-L2 antibody or fragment and other unbound substances; and (3) detecting the bound anti-PD-L2 antibody or fragment. The bound antibody or fragment may be detected by incubating the bound antibody or fragment with a secondary antibody (an anti-immunoglobulin antibody) which is detectably labeled and, then, detecting the presence of the secondary antibody.

The anti-PD-L2 antibodies and antigen-binding fragments thereof disclosed herein may also be used in immunohistochemistry (IHC) assays, which may be performed using a variety of 1IHC formats known in the art, and constitute embodiments of the invention. A typical IHC assay uses an FFPE tissue section of about 3-4 millimeters, and preferably 4 micrometers, mounted and dried on a microscope slide and comprises. e.g., (1) subjecting the tissue section to deparaffinization and hydration, contacting the rehydrated tissue section with an anti-PD-L2 antibody or antigen-binding fragment thereof of the invention; and (2) detecting the anti-PD-L2 antibody or antigen-binding fragment thereof on the surface of one or more cells in the tissue. If the antibody or fragment itself is detectably labeled, it can be detected directly. Alternatively, the antibody or fragment may be bound by a detectably labeled secondary antibody which is detected.

A preferred IHC assay employs the commercially available Dako EnVision™ FLEX detection system, which is intended for use together with a Dako Autostainer instrument (Dako, an Agilent Technologies Company, Glostrup, Denmark). When employing this system with an antibody of the invention (i.e., the 3G2 antibody, an antibody or antigen binding fragment thereof that comprises the six CDRs of 3G2, or an antibody or antigen binding fragment thereof that comprises the heavy and light chain variable regions of 3G2), the IHC assay may be performed as follows.

Assay Reagents

| Reagents | Company | Catalog # | Preparation |
|---|---|---|---|
| Anti-PD-L2 mAb | N/A | N/A | Dilute a stock solution of the mAb to 0.8 micrograms/ml with Antibody Diluent |

-continued

| Reagents | Company | Catalog # | Preparation |
|---|---|---|---|
| EnVision FLEX Kit, High pH (Plus) with Mouse Linker | Dako | K8012 | All reagents in the kit are ready to use except for:<br>EnVision FLEX Target Retrieval Solution, High pH<br>Prepared by diluting the 50X kit solution 1:50 using deionized water. Diluted solution is only good for 1 month after preparation and must be discarded if solution becomes cloudy in appearance.<br>EnVision FLEX Wash Buffer (TBST)<br>Prepared by diluting the kit 20X solution 1:20 in deionized water.<br>EnVision FLEX DAB Substrate<br>Prepared by adding 1 drop of DAB Chromogen into 1 mL of DAB Substrate Buffer. |
| Antibody Diluent | Dako | S0809 | Ready To Use |
| Mayer's Modified Hematoxylin | Poly Scientific R&D Corp. Bay Shore, NY USA | S216-1GL | Ready To Use: Filtered Daily |
| Micromount | Leica Biosystems Inc. Buffalo Grove, IL USA | 3801731 | Ready To Use |

Assay Protocol

1) Section FFPE tissues at 4 μm and allow to air dry overnight.
2) Bake slides at 60° C. for 45 minutes before use.
3) On the day of use, slides are deparaffinized using Leica Stainer XL (Program 1) which is programmed as follows:

| | | |
|---|---|---|
| 1) Xylene | 5 min x3 | |
| 2) Xylene | 3 min x1 | |
| 3) 100% Alcohol | 3 min x2 | |
| 4) 95% Alcohol | 3 min x1 | |
| 5) 95% Alcohol | 2 min x1 | |
| 6) 70% Alcohol | 2 min x1 | |
| 7) Deionized Water | 1 min x1 | |

4) Following deparaffinization. FFPE slides are subjected to heat induced epitope retrieval (HIER) using EnVision™ FLEX High pH Target Retrieval Solution at 97° C. for 20 minutes at ambient pressure.
5) The slides are then immersed in deionized water, followed by immersion two times in TBST (sections must be kept wet at all times to avoid drying artifacts).
6) The slides are then loaded into the autostainer programmed as follows:

| Step | Incubation Time | Rinses |
|---|---|---|
| EnVision Flex Peroxidase Block | 5 minutes | 1x TBST |
| Anti-PD-L2 mAb, 0.8 ug/mL | 60 minutes | 1x TBST |
| EnVision Flex + MS Linker | 15 minutes | 1x TBST |
| EnVision Flex/HRP | 20 minutes | 1x TBST |
| EnVision Flex DAB | 10 minutes | 3x Deionized Water |

7) After autostainer program is complete, slides are removed from machine, immersed in deionized water and counterstained/dehydrated using Leica Stainer XL (Program 3) which is programmed as follows:

| | |
|---|---|
| 1) Mayer's Hematoxylin | 30 sec x1 |
| 2) Deionized Water | 2 min x1 |
| 3) Richard Allen's Bluing Reagent | 20 sec x1 |
| 4) Deionized Water | 2 min x1 |
| 5) 95% Alcohol | 1 min x1 |
| 6) 100% Alcohol | 1 min x2 |
| 7) Xylene | 1 min x3 |
| 8) Xylene | Exit |

8) Slides are coverslipped with Micromount media and allowed to sufficiently dry before viewing on microscope.

Anti-PD-L2 antibodies and antigen-binding fragments thereof disclosed herein may also be used for in vivo tumor imaging. Such a method may include injection of a radio-labeled anti-PD-L2 antibody or antigen-binding fragment thereof into the body of a human patient to be tested for the presence of a tumor associated with PD-L2 expression followed by nuclear imaging of the body of the patient to detect the presence of the labeled antibody or fragment e.g., at loci comprising a high concentration of the antibody or fragment which are bound to the tumor. In an embodiment, the anti-PD-L2 antibody is a humanized antibody that comprises the six CDRs listed in Table 1. Imaging techniques include SPECT imaging (single photon emission computed tomography) or PET imaging (positron emission tomography). Labels include e.g., iodine-123 ($^{123}$I) and technetium-99m ($^{99m}$Tc). e.g., in conjunction with SPECT imaging or $^{11}$C, $^{13}$N, $^{15}$O or $^{18}$F, e.g., in conjunction with PET imaging or Indium-111 (See e.g., Gordon et al., (2005) *International Rev. Neurobiol.* 67:385-440).

Methods of Treatment

Also provided by the invention are methods for the prediction of clinical response to a PD-1 antagonist. In one embodiment, the method comprises measuring the expression level of PD-L2 in a tumor tissue sample removed from a human patient, determining if the tumor tissue sample is PD-L2 positive or negative, and administering a PD-1 antagonist to the patient if the sample is determined to be PD-L2 positive.

The invention also relates to a method for treating a patient having a tumor, the method comprising: (1) determining if the tumor is positive or negative for PD-L2 expression, and (2) administering to the subject a therapeutically effective amount of a PD-1 antagonist if the tumor is positive for PD-L2 or administering to the patient a cancer treatment that does not include a PD-1 antagonist if the tumor is negative for PD-L2.

In embodiments of the methods above, the methods further comprise determining if the tumor tissue sample is PD-L1 positive. In specific embodiments of the methods, the PD-1 antagonist is administered to the patient if the sample is determined to be positive for both PD-L1 and PD-L2.

In one embodiment of the methods above, the expression level of PD-L2 is determined through use of an anti-PD-L2 antibody, or antigen-protein fragment thereof, in an IHC assay. In embodiments of the invention, a sample is scored as "PD-L2 positive" if the level of PD-L2 expression in the IHC assay is ≥1 on a 0-5 scale, based on intensity of staining, wherein the following scale is used to classify the staining: 0=negative, 1=rare, 2=low, 3=moderate, 4=high, 5=very high. In other embodiments, a sample is scored as PD-L2 positive if the PD-L2 expression score in an IHC assay is ≥2, ≥3, ≥4 or 5.

In one embodiment of the methods above, the patient has a cancer selected from the group consisting of: non-small cell lung cancer, head and neck squamous cell carcinoma, gastric cancer, triple negative breast cancer and bladder cancer. In a specific embodiment, the patient has head and neck squamous cell carcinoma.

In one embodiment of any of the methods described above, the determining step comprises obtaining a sample from the patient's tumor; sending the tumor sample to a laboratory with a request to test the sample for the presence or absence of PD-L2: and receiving a report from the laboratory that states whether the tumor sample is PD-L2 positive or negative.

In specific embodiments of the methods described above, the PD-1 antagonist is pembrolizumab or nivolumab. In one embodiment, the PD-1 antagonist is pembrolizumab In embodiments of any of the methods described above, PD-L2 expression is determined in an IHC assay using a recombinant antigen binding protein that binds PD-L2, wherein the antibody is 3G2, or a variant thereof.

In one embodiment of the methods of invention, CDRL1 is SEQ ID NO:2 or a variant of SEQ ID NO:2, CDRL2 is SEQ ID NO:4 or a variant of SEQ ID NO:4, and CDRL3 is SEQ ID NO:6 or a variant of SEQ ID NO:6.

In one embodiment of the methods invention, the antigen binding protein comprises a $V_L$ domain comprising a CDRL1 of SEQ ID NO: 2, a CDRL2 of SEQ ID NO: 4 and a CDRL3 of SEQ ID NO: 6.

In further embodiments, the antigen binding protein used in the IHC assay comprises a $V_1$ domain comprising a sequence of amino acids as set forth in SEQ ID NO:8. In one embodiment, the $V_H$ domain consists of SEQ ID NO:8.

In one embodiment, CDRH1 is SEQ ID NO:10 or a variant of SEQ ID NO:10, CDRH2 is SEQ ID NO: 12 or a variant of SEQ ID NO:12, and CDRH3 is SEQ ID NO:14 or a variant of SEQ ID NO:14.

In one embodiment, the antigen binding protein comprises a $V_H$ domain comprising the CDRH1 set forth in SEQ ID NO: 10, the CDRH2 set forth in SEQ ID NO: 12 and the CDRH3 set forth in SEQ ID NO: 14.

In a further embodiment of the methods of the invention, the antigen binding protein comprises a $V_H$ domain comprising a sequence of amino acids as set forth in SEQ ID NO: 16. In one embodiment, the $V_H$ domain consists of SEQ ID NO: 16.

In one embodiment of the methods described above, the antigen binding protein comprises a $V_L$ domain comprising an amino acid sequence as set forth in SEQ ID NO:8 and a $V_H$ domain comprising an amino acid sequence as set forth in SEQ ID NO: 16. In a further embodiment of the invention, the antigen binding protein comprises a $V_L$ domain consisting of an amino acid sequence as set forth in SEQ ID NO:8 and a $V_H$ domain consisting of an amino acid sequence as set forth in SEQ ID NO: 16.

Also provided herein is a drug product that comprises a pharmaceutical composition and prescribing information, wherein the pharmaceutical composition comprises a PD-1 antagonist and at least one pharmaceutically acceptable excipient and the prescribing information states that the pharmaceutical composition is indicated for use in a subject who has a tumor that tests positive for PD-L2.

In embodiments of this aspect of the invention, the PD-1 antagonist is pembrolizumab.

Detection Kits and Therapeutic Kits

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments, the signal generating means may come pre-associated with an antibody of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

The detection kits disclosed herein may also be prepared that comprise at least one of the antibody or antigen-binding fragment disclosed herein and instructions for using the composition as a detection reagent. Containers for use in such kits may typically comprise at least one vial, test tube, flask, bottle, syringe or other suitable container, into which one or more of the detection composition(s) may be placed, and preferably suitably aliquoted. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection composition itself, or may alternatively be placed in a second distinct container means into which this second composition may be placed and suitably aliquoted. Alternatively, the detection reagent may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

Further embodiments also provide a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

General Methods

Standard methods in molecular biology are described Sambrook, Fritsch and Maniatis (1982 & 1989 $2^{nd}$ Edition, 2001 $3^{rd}$ Edition) *Molecular Cloning. A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.: Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science. Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science. Vol.* 2, John Wiley and Sons, Inc., New York; Ausubel, et al. (2001) *Current Protocols in Molecular Biolog, Vol.* 3. John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology. Vol.* 1, John Wiley and Sons, Inc., New York: Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology. Vol.* 4, John Wiley, Inc., New York).

Monoclonal, polyclonal, and humanized antibodies can be prepared (see, e.g., Shepard and Dean (eds.) (2000) *Monoclonal Antibodies*, Oxford Univ. Press, New York, N.Y.: Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

Antibodies can be conjugated or coupled to, e.g., small drug molecules, enzymes, liposomes, polyethylene glycol (PEG), dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons. Hoboken, N.J.; Givan (2001) *Flow Cytometry*, $2^{nd}$ ed.: Wiley-Liss, Hoboken, N.J.: Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.: Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott. Williams, and Wilkins. Phila, Pa.; Louis, et al. (2002) *Basic Histology: Text and Atlas*, McGraw-Hill, New York, N.Y.).

All references cited herein are incorporated by reference to the same extent as if each individual publication, database entry (e.g. NCBI sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

Example 1

Generation and Screening of Anti-PD-L2 Hybridomas

After tests of several commercial anti-human PD-L2 antibodies revealed them to be unsatisfactory for detecting human PD-L2 in IHC assay of FFPE tissue sections, the inventors herein conducted a series of rodent immunization campaigns to try to generate a high quality anti-human PD-L2 IHC reagent. The immunogens used in the first two campaigns were a human PD-L2-Fc fusion protein (R&D Systems: cat #: 1224-PL, Lot #: FCI051302A) and a human PD-L2-HisTag fusion protein (Sino Biologicals: cat #: 10292-H08H, Lot #: MB05OC0910). The PD-L2 Fc fusion protein contains the extracellular domain of human PD-L2 (Leu20-Pro219, NCBI Accession No. Q9BQ51.2) fused to a human IgG1 fragment. The PD-L2-HisTag fusion contains the extracellular domain of human PD-L2 fused to a polyhistidine tag. In the third campaign, the same two fusion proteins were used as immunogens after they had been denatured by boiling for 5 minutes.

Five mice were immunized in each campaign, with the PD-L2-Fc fusion being used for the first two injections and the PD-L2-HisTag used for the remainder of injections (10 to 17, depending on the campaign). In the third campaign, hybridomas were created after each of 13 and 15 immunizations.

Supernatants of the resulting hybridomas were screened to identify hybridomas that produce antibodies to human PD-L2. One of the screens employed was a protein based ELISA, which measured binding to the PD-L2-Fc, denatured PD-L2-Fc, denatured PD-L2-HisTag fusion; or an irrelevant Ig negative control (47ADY). A second screen was employed which was a cell based ELISA, which measured binding to CHO cells that had been engineered to express human PD-L2 or parental CHO cells as a negative control.

The immunization schedule and screening results are summarized in the table below.

| Campaign | No. of immunizations | Fusion | Primary screen | Secondary Screen | No. of PD-L2 positive supernatants |
|---|---|---|---|---|---|
| 1 | 19 | MEB120 | cho-PD-L2 | Cho PD-L2/Fc | 29 |
| 2 | 12 | MEB121 | cho-PD-L2 | cho PD-L2-His-Tagd* | 28 |
| 3a | 13 | MEB122 | PD-L2-His-Tagd* | Cho cho-PD-L2 PD-L2-Fcd* 47ADY | 310 |
| 3b | 15 | MEB123 | PD-L2-His-Tagd* | Cho cho-PD-L2 PD-L2-Fcd* 47ADY | 110 | d* = denatured

Hybridoma supernatants that tested positive for binding to human PD-L2 in both the primary and secondary screens were then screened for labeling of formalin-fixed, paraffin-embedded (FFPE) human normal tonsil tissue in an IHC assay. Hybridomas that had supernatants that produced no staining, nuclear staining, epithelial cell or other non-specific staining, or which had poor signal to noise ratio were rejected outright from further consideration. None of the PD-L2 binding supernatants from the first two immunization campaigns produced satisfactory IHC staining results, which prompted the inventors to employ the denatured PD-L2 fusion proteins as immunogens in the third campaign. Out of 420 hybridomas from that campaign that produced PD-L2 binding supernatants, the inventors identified only five that had sufficient labeling intensity, low background levels, and crispness of signal to be considered as candidates for use as a PD-L2 detection reagent in IHC assay. These hybridomas were then subcloned and purified for further evaluation and antibody clone 3G2 had the best performance in the criteria being evaluated.

Example 2

Materials and Methods
Staining

FFPE tissue sections were routinely deparaffinized and rehydrated for PD-L2 and PD-L1 IHC. All slides were subjected to heat-induced epitope retrieval, and endogenous peroxidase blocking was conducted prior to incubation with primary antibody (anti-PD-L2 clone 3G2 or anti-PD-L1 clone 22C3, Merck Research Laboratories, Palo Alto Calif.). Antigen-antibody binding was visualized with 3,3' diaminobenzidine (DAB) chromogen (K4368, Dako, Carpinteria Calif.).

Scoring of Archival Tumor Specimens

Archival FFPE tumor specimens were sourced from the Merck Palo Alto tissue bank. Scoring was conducted by a pathologist, with scores incorporating prevalence of both tumor cell and non-tumor cell labeling. A semi-quantitative 0-5 scoring system (0=negative, 1=rare, 2=low, 3=moderate, 4=high, 5=very high) was applied. Presence or absence of endothelial cell expression was evaluated specifically as a separate value.

In Situ Hybridization (ISH)

Cellular distribution of PD-L2 mRNA was evaluated by ISH using the RNAScope platform (RNAscope 2.0 High Definition Kit, Advanced Cell Diagnostics [ACD], Hayward Calif.) according to manufacturer's instructions. Hybridization was conducted using anti-sense and sense DNA probes for human PD-L2 (test probe and negative control, respectively) and anti-sense probe for PPIB (positive control), all designed by ACD (catalog numbers 316291, 551891, and 313901 respectively).

Gene Expression Analysis

Quantitative RT-PCR

For real-time, quantitative PCR analysis, DNase-treated total RNA was reverse-transcribed using QuantiTect Reverse Transcription (Qiagen, Valencia, Calif.) according to manufacturer's instructions. Primers specific for PDCD1LG2 (PD-L2, CD273), were obtained commercially from Applied Biosystems (Foster City, Calif.). Real-time quantitative PCR was performed on the Fluidigm Biomark using specific probe/primer mix with Taqman Universal PCR Master Mix with uracil-DNA glycosylase. Ubiquitin levels were measured in a separate reaction and used to normalize the data by the Δ Ct method.

NanoString Methodology

Tissue lysates were generated from sectioned FFPE tissue according to the manufacturer's protocol (NanoString, Seattle Wash.). Cellular lysate (50 ng per sample) was mixed with a barcoded 3' biotinylated capture probe and a fluorescently tagged 5' reporter probe from the desired gene expression codeset. Probes and target transcripts were hybridized overnight as per manufacturers' recommendations. Hybridized samples were run on the NanoString nCounter™ instrument, then samples were scanned at maximum scan resolution using the nCounter™ Digital Analyzer.

Data analysis was performed using quantile normalization in which relative ranks of genes (across all genes on the NanoString codeset) within each sample were replaced by values having the same relative rank from the pooled distribution (from all samples and genes in the dataset). All quantile normalized data underwent subsequent log 10 transformation.

Example 3

Quality Assessment of the 3G2 Anti-PD-L2 mAb

The quality of the 3G2 antibody as an IHC reagent for detection of human PD-L2 protein was tested through a series of steps, including initial screening for labeling of FFPE human normal tonsil tissue when applied at a concentration of 10 μg/mL, optimization of the assay (titration of the antibody, assessment of multiple detection systems) to generate high resolution, low background signal, and then a series of validation steps. In the validation steps, the following procedures were performed: 1) the assay was run on a panel of 37 normal human tissues, where abundant expression of PD-L2 was detected in placenta and multiple lymphoid tissues, with a corresponding isotype control for each tissue, as well as on a cohort of multiple human tumors; 2) appropriateness of the distribution of signal in tissues by IHC was cross-checked by running in situ hybridization (RNAscope, Advanced Cellular Diagnostics, Hayward Calif.) for PD-L2 mRNA on samples that had demonstrated positive signal in the IHC assay; 3) specificity of the signal generated by IHC was cross-checked by conduct of a blocking study, where tissues that had shown labeling in the IHC assay were run both routinely, and with application of the antibody to the tissue only after pre-adsorption of the antibody with immunogen to determine dependence of labeling on binding of the complementarity determining regions (CDR's) of the antibody: 4) the assay was run on FFPE cell pellets generated from a series of cell lines known to have differential levels of PD-L2 mRNA expression (CHO-K1, PD-L2 transfected CHO-K1, NCIH-226, NCIH-23, HOP-62, HOP-92, SKBR3, MCF7, M14, SR, RPMI 8226) to compare extent of signal generated by IHC to quantity of mRNA detected by conventional RNA analytic methods: and 5) the assay was run on three normal human tonsils over three days, with pathologist assessment of output comparability, to assess the reproducibility of the IHC signal. The PD-L2 IHC signal also significantly correlated with PD-L2 mRNA levels quantitated by NanoString methodology in human tumor samples ($p<0.0001$ to $p=0.0037$: data not shown).

Figure 4:
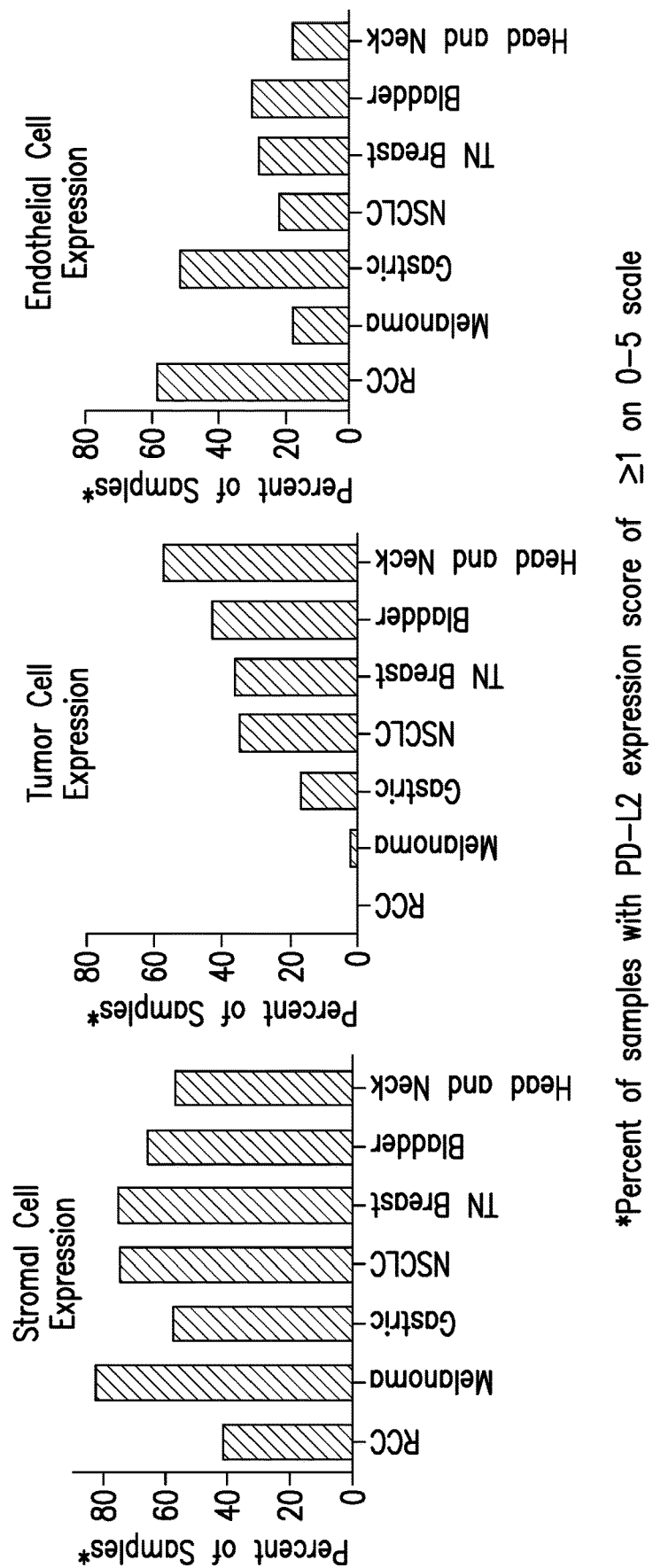
FIG. 4 illustrates PD-L2 expression by cell type in seven different tumors as detected using the 3G2 anti-PD-L2 antibody and the IHC assay described herein.

The inventors also compared the 3G2 antibody and two commercially available anti-human PD-L2 antibodies in staining of normal human tonsil tissue. The commercial antibodies used were the AF1224 polyclonal and MIH18 monoclonal antibodies described above. Adjacent FFPE tissue sections were stained using the same IHC assay conditions and the best staining results for each antibody are shown in FIG. 4 and a pathologist's evaluation of the staining results is set forth below.

3G2:

Intense crisp signal, with both round cell and dendritic morphology in germinal centers. Scattered, individuated positive cells in moderate numbers external to germinal centers. Very clean background

AF1224:

Intense round cell labeling in germinal centers, with other germinal center labeling possibly dendritic but difficult to differentiate conclusively from background. External to germinal center, mild background with no positive cell labeling clear above background.

MIH18:

Very clean labeling of population of morphologic round cells in germinal centers. No cells labeled outside germinal centers. Very clean background.

Example 4

PD-L2 Expression in Tumor and Immune Cells

To assess the utility of the 3G2 mAb for detecting PD-L2 expression in tumor tissues, archival samples of seven different tumor types were subjected to the IHC assay described herein using the 3G2 antibody. The expression of PD-L2 protein was assessed in cohorts of several tumor types including renal cell carcinoma (n=71), bladder carcinoma (n=34), melanoma (n=83), non-small cell lung cancer (NSCLC) (n=−94), HNSCC (n=40), triple negative breast cancer (TNBC) (n=22), and gastric carcinoma (n=73) by IHC staining with 3G2 anti-PD-L2 antibody (see FIG. 3). The level of PD-L2 expression was scored by a pathologist as 0 (Negative), 1 (Rare), 2 (Low), 3 (Moderate), 4 (High), or 5 (Very High) based on the intensity of staining. The inventors also analyzed results showing a range of PD-L2 expression across the different tumor types. In addition, the inventors assessed the level of PD-L2 expression in three different cell types in the tumor tissue section: stromal cells, tumor cells and endothelial cells, and the results are shown in FIG. 4. In brief, the results show that PD-L2 protein was expressed to varying degrees on stromal cells (including immune cell infiltrate), tumor cells, and endothelium, infra.

Figure 3:
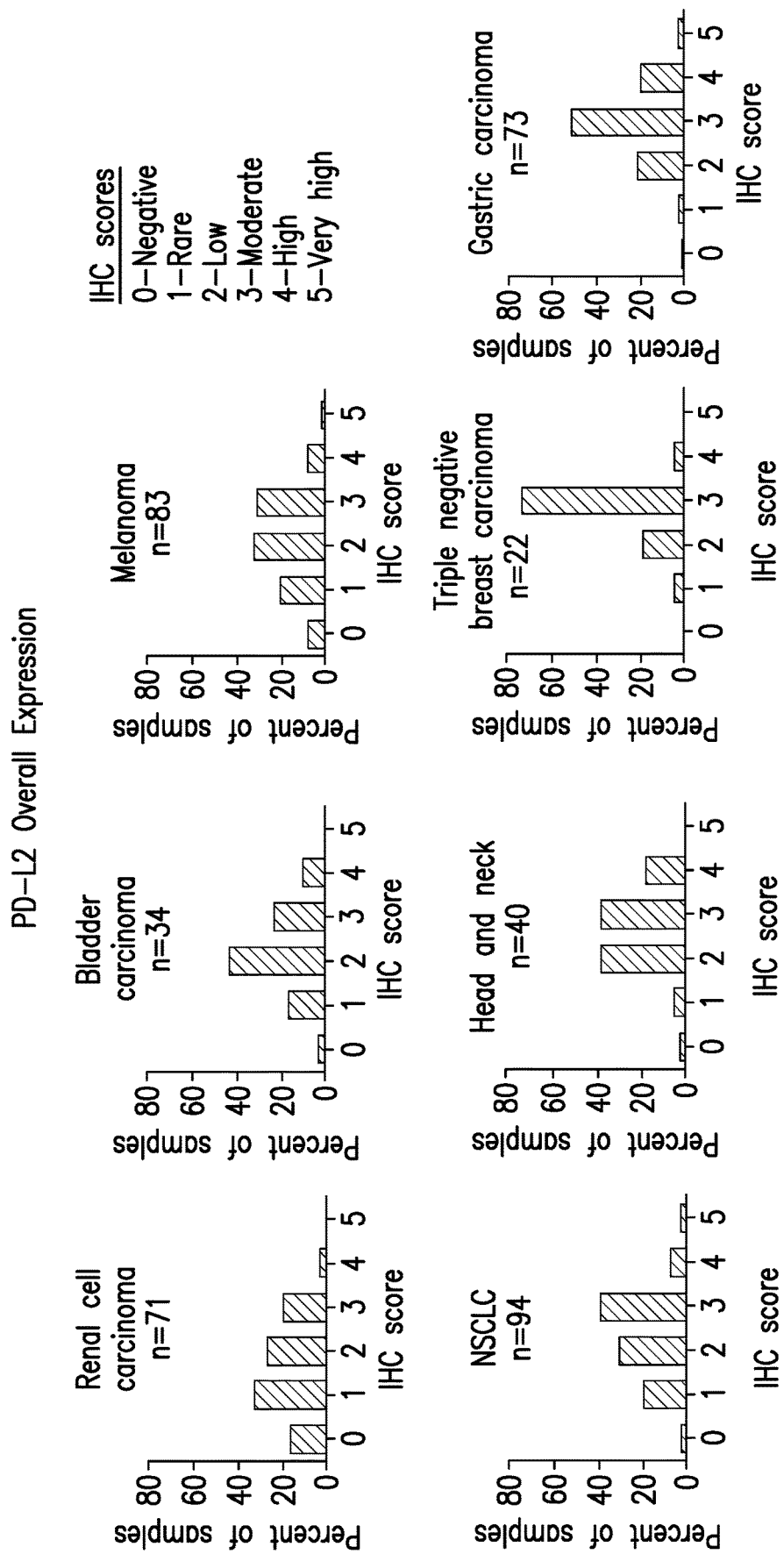
FIG. 3 illustrates PD-L2 expression in archival tissue sections from seven different cancer types as detected using the 3G2 anti-PD-L2 antibody and the IHC assay described herein.

Each cohort was evaluated for the overall prevalence of PD-L2 expression, with stromal, tumor and endothelial cells evaluated together. Although PD-L2 expression was observed in all tumor types assessed, the overall prevalence of PD-L2 expression differed by indication (FIG. 3). Renal cell carcinoma was noteworthy for a bias toward especially low overall levels of PD-L2 expression, while gastric and TNBC biased strongly toward moderate to high expression.

Expression in other tumor types distributed more evenly from low to high across evaluated samples.

When the presence or absence (scores ≥1 and <1 respectively on a 0-5 scale) of PD-L2 protein expression was evaluated by IHC staining in the three categories of stromal, tumor and endothelial cells for each tumor type, several patterns emerged (FIG. 4). The presence of PD-L2 expression in stromal cells, including immune cell infiltrate, was generally the most common and was observed across all tumor types with relatively minimal variation. In contrast, PD-L2 expression in tumor cells varied quite significantly across tumor types, with none of the renal cell carcinomas and few of the melanomas demonstrating tumor cell expression, whereas over half of the HNSCC expressed PD-L2. Finally, while endothelial cell expression was present in a minority of samples for most of the tumor types assessed, the prevalence of samples with endothelial expression was notably higher in renal cell and gastric carcinomas.

The relative prevalence and distribution of PD-L2 protein in tumor tissues in these cohorts was compared to that of PD-L1 in additional sections of the same samples, using Merck's 22C3 anti-PD-L1 IHC antibody (WO2014/100079). In general, distributional patterns and prevalence of PD-L2 closely mirrored those of PD-L1 (data not shown). However, other samples exhibited discordance between PD-L2 and PD-L1 with some showing PD-L1 signal in the absence of PD-L2, and other samples displaying PD-L2 expression in the absence of PD-L1.

Figure 5:
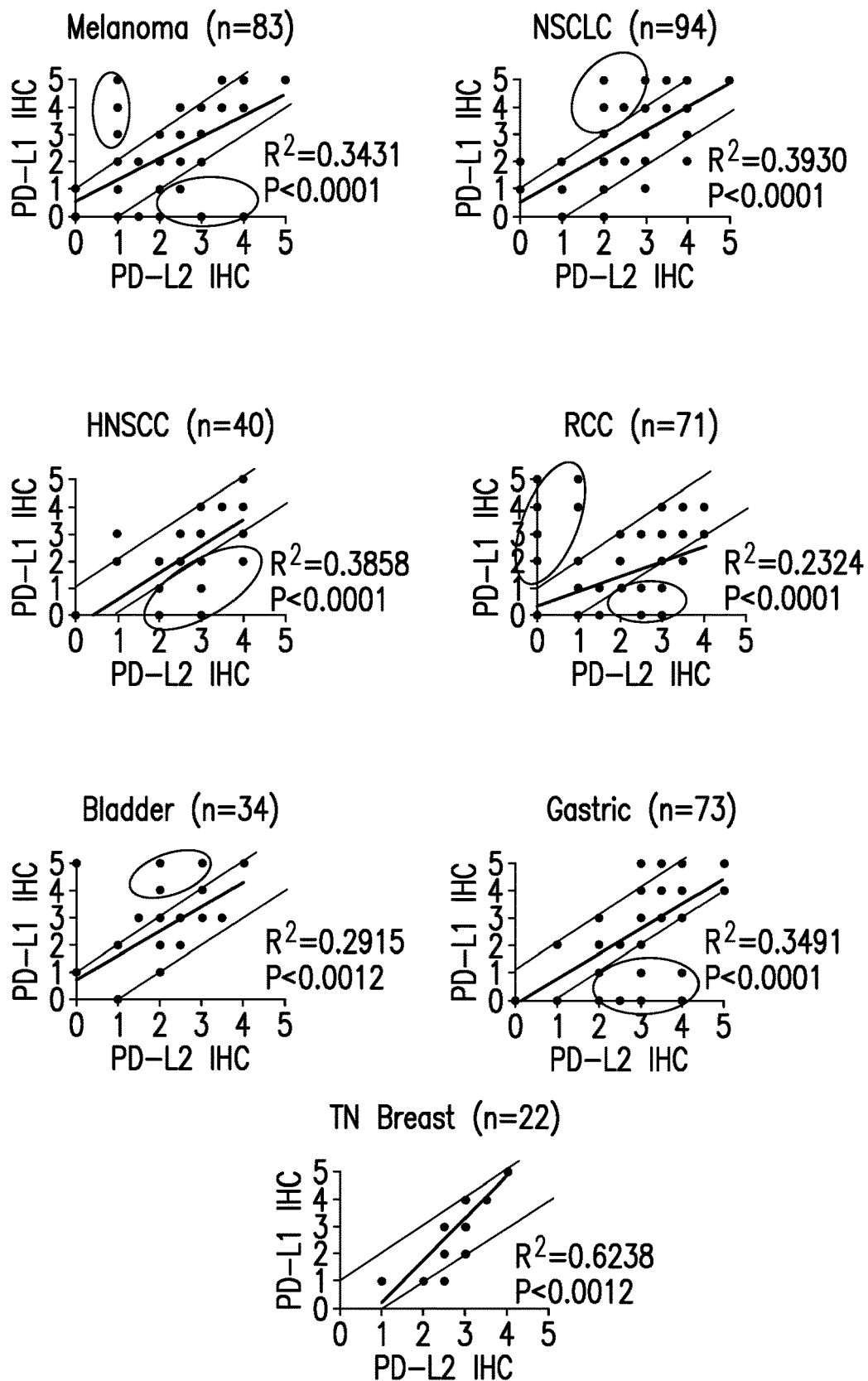
FIG. 5 shows the relationship of PD-L1 and PD-L2 in tumor types. Correlation plots of overall expression between PD-L1 and PD-L2 across all samples using the same 0 to 5 scoring system for both analytes. Scores were significantly correlated in all indications ($P=0.0012$ to $P<0.0001$.). Circles highlight samples where scores for PD-L1 and PD-L2 substantially differed.

When the overall expression of PD-L1 and PD-L2 was compared across all samples (0 to 5 scoring system for both biomarkers), the scores were found to be significantly correlated ($P=0.0012$ to $P<0.0001$) for all indications examined (FIG. 5). The strongest relationship between PD-L1 and PD-L2 ($R2=0.6238$) was observed for triple negative breast cancer (TNBC), with no significant discordance between PD-L2 and PD-L1 expression for any of the samples. For all other indications, while PD-L2 and PD-L expression scores were significantly correlated, discordant expression was observed in some samples. Bi-directional discordant expression was observed for melanoma and renal cell carcinoma, with some samples showing PD-L1 expression well in excess of PD-L2, and others displaying PD-L2 expression well in excess of PD-L1. Primarily unidirectional discordance was observed in other indications examined, with PD-L1 expressed in excess of PD-L2 in a subset of NSCLC and bladder tumor samples, but PD-L2 expressed in excess of PD-L1 in a subset of HNSCC and gastric tumor samples.

Although the expression of PD-L1 and PD-L2 was strongly correlated in all the tumor types evaluated in our analysis, PD-L2 was expressed within some tumors in the absence of PD-L1, and was independently associated with clinical response in a cohort of pembrolizumab-treated HNSCC patients when assessed in combined tumor and immune cells.

Example 5

Clinical utility of IHC Assay with the 3G2 anti-PD-L2 mAb

The relationship between PD-L1 and PD-L2 expression and clinical response to anti-PD-1 therapy was explored in tumor tissue samples from 172 HNSCC patients from the KEYNOTE-12 trial (Seiwert et al, 2016 submitted; Chow et al, 2016 submitted). Pre-treatment samples were included from HNSCC patients with recurrent or metastatic disease measurable per RECIST 1.1, ECOG performance status of 0 or 1, treated with 200 mg pembrolizumab every 3 weeks or 10/mg/kg every 2 weeks, with PD-L1 and PD-L2 IHC scoring data available. Expression for both analytes was scored using a 1% positivity cut-off (positive ≥1%; negative <1%) that included evaluation of both tumor and immune infiltrating cells. Overall response rate (ORR) was assessed in 146 of these patients in the full analysis set population defined as those who had received ≥1 dose of study drug, had a baseline disease measurement and ≥1 post-baseline scan, or who had discontinued drug due to a drug-related adverse experience or clinical progressive disease. Progression free survival (PFS) and overall survival (OS) were assessed in the 172 all-patients-as-treated population, defined as those who had received 1 dose of study drug. Relationships with PD-L2 expression were explored by logistical (ORR) or Cox (PFS, OS) regression analyses with or without adjustment for PD-L expression and with one-sided testing. Kaplan-Meier statistics were used to estimate the median survival times for PFS and OS in PD-L2 positive and negative patients.

Results

The clinical relevance of PD-L2 expression was evaluated in tumor tissue samples derived from 172 pembrolizumab-treated HNSCC patients with recurrent or metastatic disease in the KEYNOTE-12 trial, who had PD-L2 and PD-L1 IHC scoring data available. The median age of the patients sampled was 60 years (range, 37-84 years), most were men (83.1%) and a large proportion were HPV-negative (65.7%) (FIG. 6). The majority of patients were ECOG status 1 (71.5%) with metastatic staging of Ml (84.9%) and many (60.4%) had received ≥2 prior therapies for recurrent or metastatic disease.

Overall response rates were assessed as a function of PD-L1 and PD-L2 status (positivity cutoff ≥1%) in 146 patients in the full analysis set population by IHC staining in combined tumor and immune infiltrating cells. Of these, 126 (86.3%) patients had tumors that were scored as PD-L1 positive, 94 (64.3%) as PD-L2 positive, 20 (13.6%6) as PD-L1 negative and 52 (35.6%) as PD-L2 negative (FIG. 7). The response rates in the PD-L1 (23.0%; 95% CI 16.0, 31.4) and PD-L2 (26.6% 95% CI 18.0, 36.7) positive patients were significantly higher than the response rates in the PD-L1 and PD-L2 negative patients at the $p<0.05$ level (FIG. 7). Further evaluation of PD-L2 status in a logistic regression model adjusted for PD-L1 status, suggested that PD-L2 positivity provided additional predictive value for determining response ($p=0.038$), with a rate of PD-L2 positivity that was statistically significantly higher ($p<0.001$) in PD-L1 positive (72.2% [95% CI 63.5, 79.8]) than PD-L1 negative (15.0% [95% CI 3.2, 37.9] tumors. The ORR was greatest in patients who were positive for both PD-L1 and PD-L2, and was 2-fold higher (27.5% [95% CI 18.6, 37.8]) than in patients whose tumors were positive only for PD-L1 (11.4%[195% CI 3.2, 26.7]).

Figure 8A:
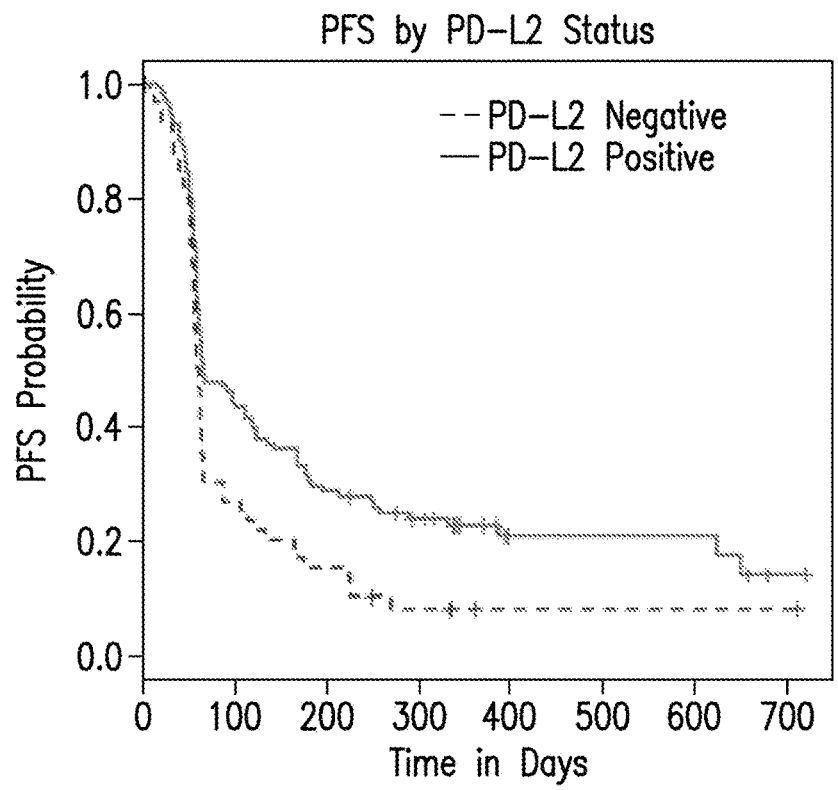
FIGS. 8A and 8B show the progression free survival and overall survival (OS) by PD-L2 status. Kaplan-Meier curve showing PFS in (FIG. 8A) and OS in (FIG. 8B) for PD-L2 positive and PD-L2 negative tumor samples (tumor and immune cells) from 172 all-patients-as-treated population in KEYNOTE-12.
Figure 8B:
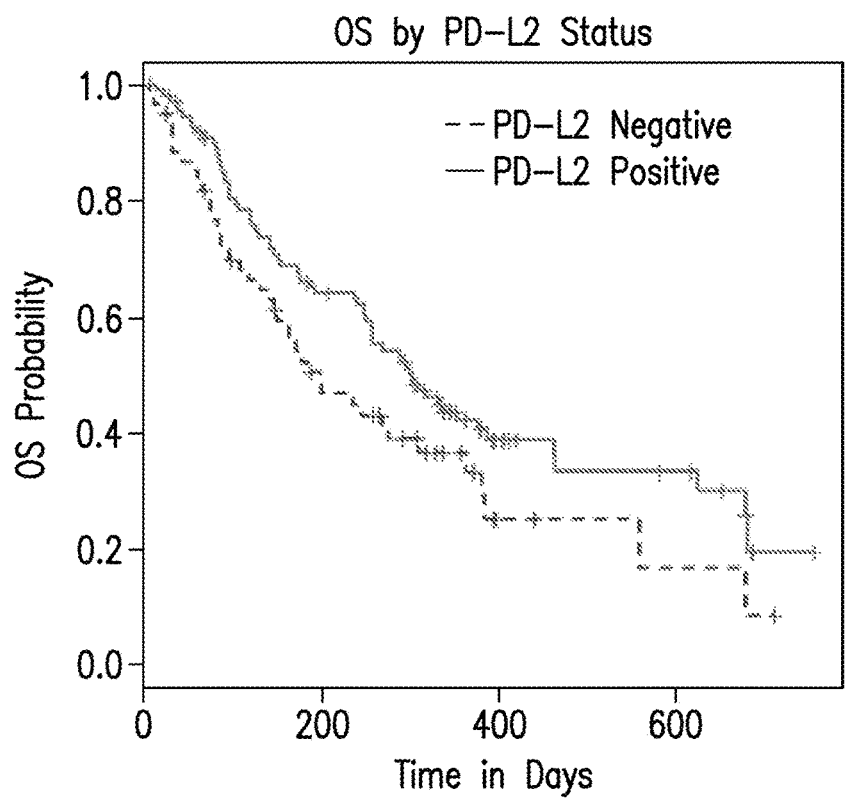

In the overall cohort of all 172 patients (all-patients-as-treated population), the relationships between PFS and PD-L and PD-L2 status were each assessed individually. PD-L1 positive status was not significantly associated with PFS ($p=0.080$). However, PD-L2 positive status was a significant predictor of PFS ($p=0.003$) and remained significantly associated with PFS after adjustment for PD-L1 status ($p=0.013$). The relationships between OS and PD-L and PD-L2 were similarly assessed. The median progression free survival times for PD-L2 negative and PD-L2 positive patients were 59 and 65 days, respectively, and median overall survival times were 199 and 303 days, respectively (FIG. 8).

These data suggest that PD-L2 expression is associated with a higher objective response rate (ORR) after adjusting for PD-L1 expression and that PD-L2 is positively associated with longer progression free survival (PFS) after adjusting for impact of PD-L1 status. This suggests that anti-PD1 therapies, which target both PD-L1 and PD-L2, may have benefits over anti-PD-L1 targeted agents in some contexts where PD-L2 expression is present.

What is claimed:

1. An isolated antibody or antigen binding fragment thereof that specifically binds human PD-L2 and comprises three light chain CDRs of CDRL1, CDRL2 and CDRL3 and three heavy chain CDRs of CDRH1, CDRH2 and CDRH3, wherein:
   (a) CDRL1 is the amino acid sequence of SEQ ID NO:2;
   (b) CDRL2 is the amino acid sequence of SEQ ID NO:4;
   (c) CDRL3 is the amino acid sequence of SEQ ID NO:6;
   (d) CDRH1 is the amino acid sequence of SEQ ID NO:10;
   (e) CDRH2 is the amino acid sequence of SEQ ID NO:12; and
   (f) CDRH3 is the amino acid sequence of SEQ ID NO:14.

2. The isolated antibody or antigen binding fragment thereof of claim 1, which comprises a light chain variable region and a heavy chain variable region, wherein:
   (a) the light chain variable region comprises the amino acid sequence of SEQ ID NO:8 or a variant of SEQ ID NO:8 wherein the variation occurs in the framework region of the light chain variable region; and
   (b) the heavy chain variable region comprises the amino acid sequence of SEQ ID NO:16 and a variant of SEQ ID NO:16 wherein the variation occurs in the framework region of the heavy chain variable region.

3. The isolated antibody or antigen binding fragment thereof of claim 2, which comprises a light chain variable region and a heavy chain variable region, wherein the light chain variable region is SEQ ID NO:8 and the heavy chain variable region is SEQ ID NO:16.

4. The isolated antibody of claim 3, which comprises a mouse $IgG_1$ constant region.

5. The isolated antibody of claim 3, which comprises two identical heavy chains and two identical light chains, wherein each heavy chain comprises a mouse $IgG_1$ constant region and each light chain comprises a mouse kappa constant region.

6. An isolated nucleic acid which encodes one or both of an antibody light chain variable region and an antibody heavy chain variable region, wherein the antibody light chain variable region comprises the amino acid sequence of SEQ ID NO:8 and the antibody heavy chain variable region comprises the amino acid sequence of SEQ ID NO:16.

7. The isolated nucleic acid of claim 6, which comprises one or both of SEQ ID NO:17 and SEQ ID NO:18.

8. An expression vector comprising the isolated nucleic acid of claim 6.

9. A method of assaying a tissue sample removed from a human for PD-L2 expression, the method comprising:
   (a) contacting the tissue sample with a PD-L2 binding reagent under conditions that allow specific binding of the PD-L2 binding reagent to human PD-L2, wherein the binding reagent comprises the antibody or antigen binding fragment of claim 1,
   (b) removing unbound PD-L2 binding reagent, and
   (c) detecting the presence or absence of bound PD-L2 binding agent.

10. The method of claim 9, which further comprises quantifying the amount of bound binding reagent.

11. The method of claim 9, wherein the binding reagent comprises two identical heavy chains and two identical light chains, wherein each heavy chain comprises the amino acid sequence of SEQ NO:16 and a mouse $IgG_1$ constant region and each light chain comprises the amino acid sequence of SEQ ID NO:8 and a mouse kappa constant region.

12. The method of claim 11, wherein the tissue sample is from a tumor.

13. The method of claim 10, wherein the tissue sample is from a tumor and the patient is diagnosed with bladder cancer, gastric cancer, head and neck squamous cell cancer, melanoma, non-small cell lung cancer, renal cell cancer, or triple negative breast cancer.

14. A kit comprising the isolated antibody or antigen binding fragment thereof of claim 1 and a set of reagents for detecting a complex of the antibody or the antigen binding fragment bound to human PD-L2.

15. The kit of claim 14, wherein the antibody comprises two identical heavy chains and two identical light chains, wherein each heavy chain comprises the amino acid sequence of SEQ NO:16 and a mouse $IgG_1$ constant region and each light chain comprises the amino acid sequence of SEQ ID NO:8 and a mouse kappa constant region.

16. A method for treating a patient having a tumor, the method comprising:
   (1) determining if a sample from the tumor is positive or negative for PD-L2 expression using the method of claim 9; and
   (2) administering to the subject a therapeutically effective amount of a PD-1 antagonist if the tumor is positive for PD-L2.

17. The method of claim 16, further comprising a step of determining if the tumor tissue sample is positive for PD-L1 expression and the PD-1 antagonist is administered to the patient if the sample is determined to be positive for both PD-L1 and PD-L2.

18. The method of claim 16, wherein the PD-1 antagonist is pembrolizumab.

* * * * *